US011941805B2

(12) United States Patent
Lyu

(10) Patent No.: US 11,941,805 B2
(45) Date of Patent: Mar. 26, 2024

(54) SYSTEMS AND METHODS FOR IMAGE PROCESSING

(71) Applicant: SHANGHAI UNITED IMAGING HEALTHCARE CO., LTD., Shanghai (CN)

(72) Inventor: Yang Lyu, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 247 days.

(21) Appl. No.: 17/305,946

(22) Filed: Jul. 17, 2021

(65) Prior Publication Data
US 2022/0020146 A1 Jan. 20, 2022

(30) Foreign Application Priority Data
Jul. 17, 2020 (CN) .......................... 202010689748.2

(51) Int. Cl.
*G06T 7/00* (2017.01)
*G06N 20/00* (2019.01)
(Continued)

(52) U.S. Cl.
CPC ............ *G06T 7/0012* (2013.01); *G06N 20/00* (2019.01); *G06T 5/002* (2013.01); *G06T 5/20* (2013.01);
(Continued)

(58) Field of Classification Search
CPC ......... G06T 7/0012; G06T 5/002; G06T 5/20; G06T 5/50; G06T 2207/20081;
(Continued)

(56) References Cited

U.S. PATENT DOCUMENTS 10,878,576 B2 * 12/2020 Han ........................ G06T 7/11
11,132,775 B2 * 9/2021 Hwang ................... G06N 3/08
(Continued)

FOREIGN PATENT DOCUMENTS

CN 106097257 A 11/2016

OTHER PUBLICATIONS

Eugene J. Teoh et al., Phantom and Clinical Evaluation of the Bayesian Penalized Likelihood Reconstruction Algorithm Q.Clear on an LYSO PET/CT System, The Journal of Nuclear Medicine, 56(9): 1447-1452, 2015.
(Continued)

*Primary Examiner* — Edward F Urban
*Assistant Examiner* — Benedict E Lee
(74) *Attorney, Agent, or Firm* — METIS IP LLC

(57) ABSTRACT

The present disclosure relates to systems and methods for image processing. The methods may include obtaining imaging data of a subject, generating a first image based on the imaging data, and generating at least two intermediate images based on the first image. At least one of the at least two intermediate images may be generated based on a machine learning model. And the at least two intermediate images may include a first intermediate image and a second intermediate image. The first intermediate image may include feature information of the first image, and the second intermediate image may have lower noise than the first image. The methods may further include generating, based on the first intermediate image and at least one of the first image or the second intermediate image, a target image of the subject.

19 Claims, 12 Drawing Sheets

(51) Int. Cl.
*G06T 5/00* (2006.01)
*G06T 5/20* (2006.01)
*G06T 5/50* (2006.01)
*G06V 10/46* (2022.01)

(52) U.S. Cl.
CPC .............. *G06T 5/50* (2013.01); *G06V 10/462* (2022.01); *G06T 2207/20081* (2013.01)

(58) Field of Classification Search
CPC . G06T 2207/10072; G06T 2207/20084; G06T 2207/20221; G06T 2207/30004; G06T 11/003; G06T 11/006; G06N 20/00; G06N 3/045; G06N 3/047; G06N 3/084; G06N 3/08; G06V 10/462; G06V 2201/03; G06V 10/82; G06V 20/20; G16H 30/20; G16H 30/40; G16H 40/67; G16H 50/20; G16H 50/70
See application file for complete search history.

(56) References Cited

U.S. PATENT DOCUMENTS

| | | | | |
|---|---|---|---|---|
| 11,222,406 B2* | 1/2022 | Sharma | ...................... | G06T 5/50 |
| 11,645,735 B2* | 5/2023 | Liu | .......................... | G06T 5/50 |
| | | | | 382/155 |
| 2010/0134693 A1 | 6/2010 | Lee et al. | | |
| 2016/0125576 A1 | 5/2016 | Sonoda | | |
| 2017/0213364 A1 | 7/2017 | Sperl et al. | | |
| 2019/0251694 A1 | 8/2019 | Han et al. | | |
| 2019/0385044 A1* | 12/2019 | Fujimura | .............. | G06F 18/211 |
| 2020/0211178 A1* | 7/2020 | Zhou | .................... | G06V 10/993 |
| 2020/0296305 A1* | 9/2020 | Weng | .................... | H04N 17/002 |
| 2021/0150668 A1* | 5/2021 | Kim | ...................... | G06T 3/4038 |
| 2021/0312637 A1* | 10/2021 | Zhang | ..................... | G06T 7/136 |
| 2022/0058803 A1* | 2/2022 | Bhattacharya | ............ | G06T 5/50 |
| 2022/0301714 A1* | 9/2022 | Kim | ...................... | A61B 6/5217 |

OTHER PUBLICATIONS

Yang, Bao et al., Artificial Neural Network Enhanced Bayesian PET Image Reconstruction, IEEE Transactions on Medical Imaging, 2018, 34 pages.

Gong, Kuang et al., Iterative PET Image Reconstruction Using Convolutional Neural Network Representation, IEEE Transactions on Medical Imaging, 38(3): 675-685, 2019.

Hongki Lim et al., Improved Low-Count Quantitative PET Reconstruction with an Iterative Neural Network, IEEE Transactions on Medical Imaging, 39(11): 3512-3522, 2020.

Gong, Kuang et al., PET Image Reconstruction Using Deep Image Prior, IEEE Transactions on Medical Imaging, 38(7): 1655-1665, 2019.

* cited by examiner

SYSTEMS AND METHODS FOR IMAGE PROCESSING

CROSS-REFERENCE TO RELATED APPLICATIONS

This application claims priority of Chinese Patent Application No. 202010689748.2 filed on Jul. 17, 2020, the contents of which are incorporated herein by reference.

TECHNICAL FIELD

The present disclosure generally relates to medical imaging, and in particular, to systems and methods for image processing.

BACKGROUND

A medical imaging scan may be performed using any one of a plurality of scanning systems, such as a magnetic resonance (MR) imaging system, a computed tomography (CT) imaging system, an X-ray imaging system, a positron emission tomography (PET) imaging system, a digital radiography (DR) system, or the like, or any combination thereof. During a medical imaging scan, a relatively low detected count may be used in certain scenarios, such as a low-dose imaging of a radiation-sensitive subject, imaging using ultra-long half-life/ultra-short half-life drugs, a high-temporal resolution dynamic imaging, or the like, which may cause relatively high noise in images reconstructed based on imaging data so acquired.

SUMMARY

An aspect of the present disclosure relates to a method for image processing. The method may be implemented on a computing device having at least one storage device storing a set of instructions, and at least one processor in communication with the at least one storage device. The method may include obtaining imaging data of a subject, generating a first image based on the imaging data, and generating at least two intermediate images based on the first image. At least one of the at least two intermediate images may be generated based on a machine learning model. And the at least two intermediate images may include a first intermediate image and a second intermediate image. The first intermediate image may include feature information of the first image, and the second intermediate image may have lower noise than the first image. The method may further include generating, based on the first intermediate image and at least one of the first image or the second intermediate image, a target image of the subject.

In some embodiments, the generating a first image based on the imaging data may include generating the first image by performing, based on the imaging data, a projection operation.

In some embodiments, the generating a first image based on the imaging data may include generating the first image by performing, based on the imaging data, a transformation operation.

In some embodiments, the first intermediate image may be generated by extracting the feature information of the first image.

In some embodiments, the feature information may include at least one of: gradient information, or grayscale information.

In some embodiments, the extracting the feature information of the first image may include generating a feature map based on the first image, and determining the feature information of the first image based on the feature map.

In some embodiments, the generating a feature map based on the first image may include obtaining a second-order differential value and a pixel mean value of the first image, and generating the feature map based on the second-order differential value and the pixel mean value.

In some embodiments, the extracting the feature information of the first image may include determining the feature information of the first image based on a first machine learning model.

In some embodiments, the second intermediate image may be generated by performing a filtering operation on the first image.

In some embodiments, the second intermediate image may be generated by processing, based on a second machine learning model, the first image.

In some embodiments, the second machine learning model may be generated according to a model training process. The model training process may include obtaining a training sample set including a plurality of sample image pairs. Each of the plurality of sample image pairs may include a first sample image and a second sample image of a same sample subject. The first sample image may have lower noise than the second sample image. And the model training process may further include training a preliminary second machine learning model based on the training sample set.

In some embodiments, the generating the second intermediate image by processing, based on a second machine learning model, the first image may include generating, based on an initial image, a third image using the second machine learning model, determining loss information between the first image and the third image, updating the second machine learning model based on the loss information, and generating, based on the first image, the third image using the updated second machine learning model.

In some embodiments, the generating, based on the first intermediate image and at least one of the first image or the second intermediate image, a target image of the subject may include determining a first weight for the first intermediate image, determining a second weight for the first image, and generating the target image by combining, based on the first weight and the second weight, the first intermediate image and the first image.

In some embodiments, the first weight may be larger than the second weight.

In some embodiments, the generating, based on the first intermediate image and at least one of the first image or the second intermediate image, a target image of the subject may include determining a first weight for the first intermediate image, determining a second weight for the second intermediate image, and generating the target image by combining, based on the first weight and the second weight, the first intermediate image and the second intermediate image.

In some embodiments, the first weight may be larger than the second weight.

In some embodiments, the method may further include updating the target image according to an iterative operation including one or more iterations.

Another aspect of the present disclosure relates to a method for image processing. The method may be implemented on a computing device having at least one storage device storing a set of instructions, and at least one processor in communication with the at least one storage device. The method may include obtaining imaging data of a subject, generating a first image based on the imaging data, generating a first intermediate image by extracting feature information of the first image, generating a second intermediate image by processing, based on a machine learning model, the first image, and generating, based on the first intermediate image and the second intermediate image, a target image of the subject.

In some embodiments, the machine learning model may be generated according to a model training process. The model training process may include obtaining a training sample set including a plurality of sample image pairs. Each of the plurality of sample image pairs may include a first sample image and a second sample image of a same sample subject. The first sample image may have lower noise than the second sample image. And the model training process may further include training a preliminary machine learning model based on the training sample set.

A further aspect of the present disclosure relates to a system for imaging processing. The system may include at least one storage medium including a set of instructions, and at least one processor in communication with the at least one storage medium. When executing the set of instructions, the at least one processor may be directed to cause the system to perform operations. The operations may include obtaining imaging data of a subject, generating a first image based on the imaging data, and generating at least two intermediate images based on the first image. At least one of the at least two intermediate images may be generated based on a machine learning model. And the at least two intermediate images may include a first intermediate image and a second intermediate image. The first intermediate image may include feature information of the first image, and the second intermediate image may have lower noise than the first image. And the operations may further include generating, based on the first intermediate image and at least one of the first image or the second intermediate image, a target image of the subject.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
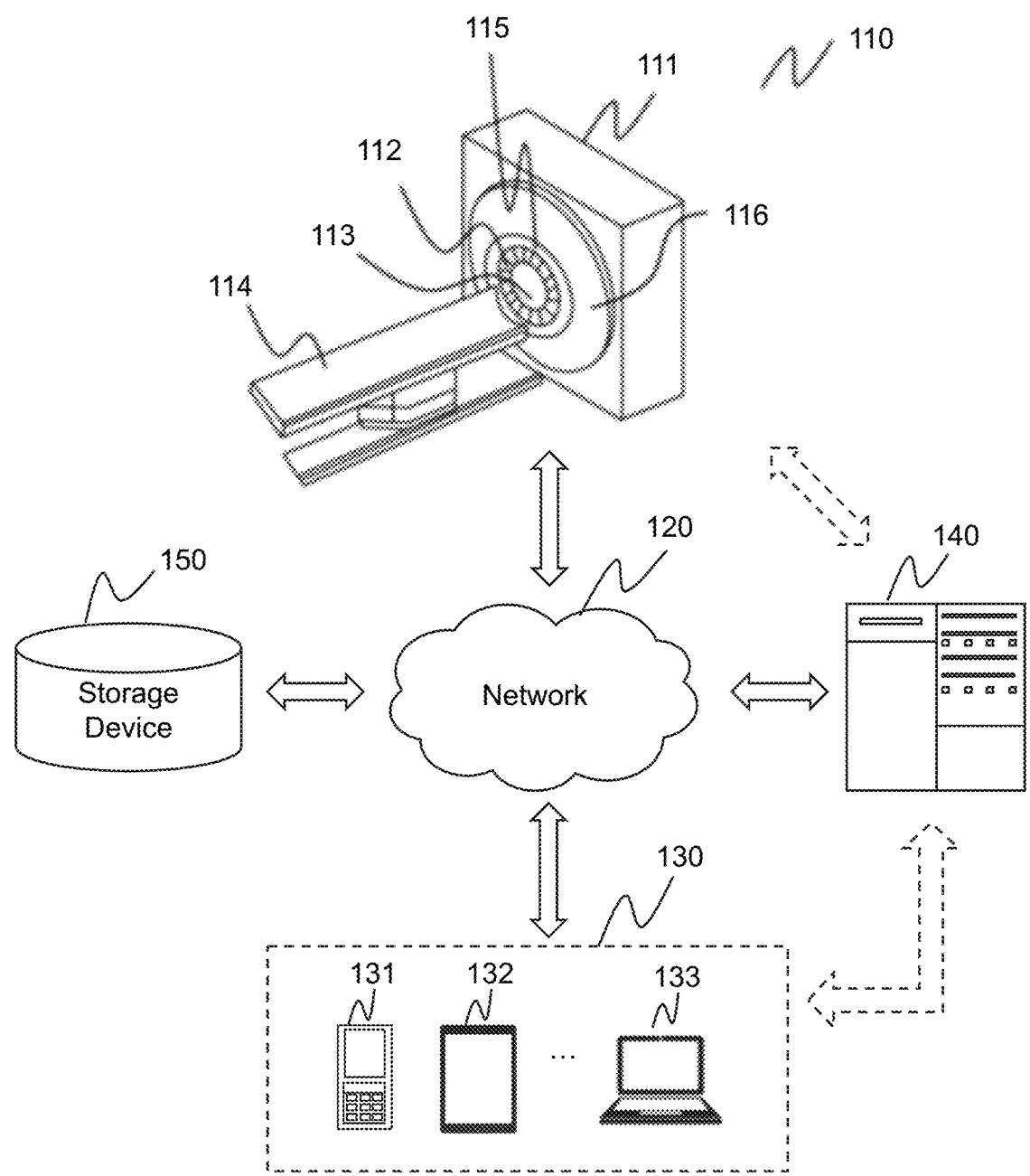
FIG. 1 is a schematic diagram illustrating an exemplary imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this disclosure, specify the presence of stated features, integers, steps, operations, elements, and/or components, but do not preclude the presence or addition of one or more other features, integers, steps, operations, elements, components, and/or groups thereof.

It will be understood that the terms "system," "engine," "unit," "module," and/or "block" used herein are one method to distinguish different components, elements, parts, sections, or assemblies of different levels in ascending order. However, the terms may be displaced by another expression if they achieve the same purpose.

Generally, the words "module," "unit," or "block" used herein refer to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for performing on computing devices (e.g., processor 220 illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to performing). Such software code may be stored, partially or fully, on a storage device of the performing computing device, for performing by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module, or block is referred to as being "on," "connected to," or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. The term "image" in the present disclosure is used to collectively refer to imaging data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image. The term "region," "location," and "area" in the present disclosure may refer to a location of an anatomical structure shown in the image or an actual location of the anatomical structure existing in or on a target subject's body, since the image may indicate the actual location of a certain anatomical structure existing in or on the target subject's body.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

Provided herein are systems and components for medical imaging and/or medical treatment. In some embodiments, the medical system may include an imaging system. The imaging system may include a single modality imaging system and/or a multi-modality imaging system. The single modality imaging system may include, for example, a magnetic resonance imaging (MRI) system, a positron emission tomography (PET) system, an emission computed tomography (ECT) system, a computed tomography (CT) imaging system, an X-ray imaging system, a molecular imaging (MI) system, a radiation therapy (RT) system, or the like, or any combination thereof. The multi-modality imaging system may include, for example, a computed tomography-magnetic resonance imaging (MRI-CT) system, a positron emission tomography-magnetic resonance imaging (PET-MRI) system, a single photon emission computed tomography-magnetic resonance imaging (SPECT-MRI) system, a digital subtraction angiography-magnetic resonance imaging (DSA-MRI) system, a computed tomography-positron emission tomography (CT-PET) system, or the like, or any combination thereof. In some embodiments, the medical system may include a treatment system. The treatment system may include a treatment plan system (TPS), image-guided radiotherapy (IGRT), etc. The image-guided radiotherapy (IGRT) may include a treatment device and an imaging device. The treatment device may include a linear accelerator, a cyclotron, a synchrotron, etc., configured to perform a radiotherapy on a subject. The treatment device may include an accelerator of species of particles including, for example, photons, electrons, protons, or heavy ions. The imaging device may include an MRI scanner, a CT scanner (e.g., cone beam computed tomography (CBCT) scanner), a digital radiology (DR) scanner, an electronic portal imaging device (EPID), etc.

The present disclosure may provide systems and methods for image processing. The systems may obtain imaging data (e.g., scanning data) of a subject (e.g., a patient). The systems may generate a first image based on the imaging data. The systems may generate at least two intermediate images based on the first image. At least one of the at least two intermediate images may be generated based on a machine learning model. The at least two intermediate images may include a first intermediate image and a second intermediate image. The first intermediate image may include feature information of the first image, and the second intermediate image may have lower noise than the first image. The system may further generate, based on the first intermediate image and at least one of the first image or the second intermediate image, a target image of the subject. According to some embodiments of the systems and methods of the present disclosure, feature information (e.g., gradient information, gray scale information, etc.) in the first image is retained in the first intermediate image, and noise in the first image is reduced in the second intermediate image. The first intermediate image and the second intermediate image (or the first image) are combined to generate the target image, which may improve the image quality and signal-to-noise ratio of the target image.

The following description is provided to facilitate a better understanding of systems and/or methods for regularized image reconstruction. The description in connection with data relating to the imaging system described below is merely provided as an example, and not intended to limit the scope of the present disclosure. For persons having ordinary skills in the art, the systems and methods disclosed herein may be applied to any other systems and/or devices for image processing.

FIG. 1 is a schematic diagram illustrating an exemplary imaging system according to some embodiments of the present disclosure. As illustrated, the imaging system 100 may include an imaging device 110, a network 120, a terminal device 130, a processing device 140, and a storage device 150. The components of the imaging system 100 may be connected in one or more of various ways. For example, the imaging device 110 may be connected to the processing device 140 through the network 120. As another example, the imaging device 110 may be connected to the processing device 140 directly (as indicated by the bi-directional arrow in dotted lines linking the imaging device 110 and the processing device 140). As a further example, the storage device 150 may be connected to the processing device 140 directly or through the network 120. As still a further example, the terminal device 130 may be connected to the processing device 140 directly (as indicated by the bi-directional arrow in dotted lines linking the terminal device 130 and the processing device 140) or through the network 120.

The imaging device 110 may scan a subject located within its detection region and generate or acquire data relating to the subject. For example, the imaging device 110 may scan the subject and generate scan data relating to the brain of the subject. In some embodiments, the subject may include a biological subject and/or a non-biological subject. For example, the subject may include a specific portion of a body, such as the head, the thorax, the abdomen, or the like, or a combination thereof. As another example, the subject may be a man-made composition of organic and/or inorganic matters that are with or without life. In some embodiments, the imaging system 100 may include modules and/or components for performing imaging and/or related analysis. In some embodiments, the data relating to the subject may include projection data, scanning data, one or more images of the subject, etc.

In some embodiments, the imaging device 110 may be a medical imaging device for disease diagnostic or research purposes. The medical imaging device may include a single modality scanner and/or a multi-modality scanner. The single modality scanner may include, for example, an ultrasound scanner, an X-ray scanner, an computed tomography (CT) scanner, a magnetic resonance imaging (MRI) scanner, an ultrasonography scanner, a positron emission tomography (PET) scanner, an optical coherence tomography (OCT) scanner, an ultrasound (US) scanner, an intravascular ultrasound (IVUS) scanner, a near infrared spectroscopy (NIRS) scanner, a far infrared (FIR) scanner, or the like, or any combination thereof. The multi-modality scanner may include, for example, an X-ray imaging-magnetic resonance imaging (X-ray-MRI) scanner, a positron emission tomography-X-ray imaging (PET-X-ray) scanner, a single photon emission computed tomography-magnetic resonance imaging (SPECT-MRI) scanner, a positron emission tomography-computed tomography (PET-CT) scanner, a digital subtraction angiography-magnetic resonance imaging (DSA-MRI) scanner, etc. It should be noted that the scanner described above is merely provided for illustration purposes, and not intended to limit the scope of the present disclosure. The term "imaging modality" or "modality" as used herein broadly refers to an imaging method or technology that gathers, generates, processes, and/or analyzes imaging information of a target subject.

In some embodiments, the imaging device 110 may include a supporting assembly 111 (e.g., a gantry), a detector assembly 112, a scanning table 114, an electronic module 115, and a cooling assembly 116.

The supporting assembly 111 may support one or more components of the imaging device 110 including, e.g., the detector assembly 112, the electronic module 115, the cooling assembly 116, etc. In some embodiments, the supporting assembly 111 may include a main gantry, a gantry base, a front cover plate, and a rear cover plate (not shown). The front cover plate may be connected to the gantry base. The front cover plate may be substantially perpendicular to the gantry base. As used herein, "substantially" indicates that a deviation (e.g., a deviation from being perpendicular) is below a threshold. For instance, the deviation of the angle between the front cover plate and the gantry base from 90° may be below a threshold, e.g., 10°, 8°, 5°, etc. The front cover plate may be mounted on the main gantry. The main gantry may include one or more supporting frames to accommodate the detector assembly 112 and/or the electronic module 115. The main gantry may include a substantially circular opening (e.g., a detection region 113) to accommodate a subject for scanning. In some embodiments, the opening of the main gantry may have another shape including, for example, an oval. The rear cover plate may be mounted on the main gantry opposing the front cover plate. The gantry base may support the front cover plate, the main gantry, and/or the rear cover plate. In some embodiments, the imaging device 110 may include a casing configured to cover and protect the main gantry.

The detector assembly 112 may detect radiation events (e.g., gamma photons) emitted from the detection region 113. In some embodiments, the detector assembly 112 may receive radiation rays (e.g., gamma rays) impinging on the detector assembly 112 and generate electrical signals. The detector assembly 112 may include one or more detector units. The one or more detector units may be packaged to form a detector block. One or more detector blocks may be packaged to form a detector cassette. One or more detector cassettes may be arranged to form a detector module. One or more detector modules may be arranged to form a detector ring.

The electronic module 115 may collect and/or process the electrical signals generated by the detector assembly 112. The electronic module 115 may include an adder, a multiplier, a subtracter, an amplifier, a drive circuit, a differential circuit, an integral circuit, a counter, a filter, an analog-to-digital converter (ADC), a lower limit detection (LLD) circuit, a constant fraction discriminator (CFD) circuit, a time-to-digital converter (TDC), a coincidence circuit, or the like, or any combination thereof. The electronic module 115 may convert an analog signal relating to an energy of radiation rays received by the detector assembly 112 to a digital signal. The electronic module 115 may compare a plurality of digital signals, analyze the plurality of digital signals, and determine imaging data based on the energies of radiation rays received by the detector assembly 112.

Merely by way of example, if the detector assembly 112 is part of a PET scanner that has a large (or long) axial field of view (FOV) (e.g., 0.75 meters to 2 meters long), the electronic module 115 may have a high data input rate from multiple detector channels. The electronic module 115 may collect the electrical signals from the detector assembly 112 through the detector channels. For example, the electronic module 115 may handle up to tens of billion events per second. In some embodiments, the data input rate may relate to a count of detector units in the detector assembly 112.

The cooling assembly 116 may produce, transfer, deliver, channel, or circulate a cooling medium to the imaging device 110 to absorb heat produced by the imaging device 110 during an imaging procedure. In some embodiments, the cooling assembly 116 may be entirely integrated into the imaging device 110 and be a part of the imaging device 110. In some embodiments, the cooling assembly 116 may be partially integrated into the imaging device 110. For example, a portion of the cooling assembly 116 may be integrated into the imaging device 110, while another portion of the cooling assembly 116 may be configured outside the imaging device 110. The cooling assembly 116 may allow the imaging device 110 to maintain a suitable and stable working temperature (e.g., 25° C., 30° C., 35° C., etc.). In some embodiments, the cooling assembly 116 may control the temperature of one or more target components of the imaging device 110. The target components may include the detector assembly 112, the electronic module 115, and/or any other components that generate heat in operation. The cooling medium may be gaseous, liquid (e.g., water), or the like, or any combination thereof. In some embodiments, the gaseous cooling medium may be air.

The network 120 may include any suitable network that can facilitate the exchange of information and/or data for the imaging system 100. In some embodiments, one or more components (e.g., the imaging device 110, the terminal device 130, the processing device 140, the storage device 150) of the imaging system 100 may communicate with one or more other components of the imaging system 100 via the network 120. For example, the processing device 140 may obtain imaging data from the imaging device 110 via the network 120. In some embodiments, the network 120 may be any type of wired or wireless network, or a combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal device 130 may include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smart watch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google™ Glass, an Oculus Rift, a Hololens, a Gear VR, etc. In some embodiments, the imaging device 110 and/or the processing device 140 may be remotely operated through the terminal device 130. In some embodiments, the imaging device 110 and/or the processing device 140 may be operated through the terminal device 130 via a wireless connection. In some embodiments, the terminal device 130 may receive information and/or instructions inputted by a user, and send the received information and/or instructions to the imaging device 110 or the processing device 140 via the network 120. In some embodiments, the terminal device 130 may receive data and/or information from the processing device 140. In some embodiments, the terminal device 130 may be part of the processing device 140. In some embodiments, the terminal device 130 may be omitted.

The processing device 140 may process data and/or information obtained from the imaging device 110, the terminal device 130, the storage device 150, and/or any other components associated with the imaging system 100. For example, the processing device 140 may process imaging data obtained from the imaging device 110 or the storage device 150. Merely by way of example, the processing device 140 may generate a first image based on the imaging data. The processing device 140 may further generate at least two intermediate images based on the first image. Further, the processing device 140 may further control other components in the imaging system 100 based on the data, the information, and/or processing results. For example, the processing device 140 may generate a target image based on the at least two intermediate images. In some embodiments, the processing device 140 may be a single server or a server group. The server group may be centralized or distributed. In some embodiments, the processing device 140 may be local or remote. For example, the processing device 140 may access information and/or data stored in or acquired by the imaging device 110, the terminal device 130, the storage device 150, and/or any other components associated with the imaging system 100 via the network 120. As another example, the processing device 140 may be directly connected to the imaging device 110 (as illustrated by the bidirectional arrow in dashed lines connecting the processing device 140 and the imaging device 110 in FIG. 1), the terminal device 130 (as illustrated by the bidirectional arrow in dashed lines connecting the processing device 140 and the terminal device 130 in FIG. 1), and/or the storage device 150 to access stored or acquired information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 having one or more components illustrated in FIG. 2 in the present disclosure.

The storage device 150 may store data and/or instructions. In some embodiments, the storage device 150 may store data obtained from the imaging device 110, the terminal device 130, and/or the processing device 140. For example, the storage device 150 may store imaging data of a subject acquired by the imaging device 110. As another example, the storage device 150 may store a machine learning model used for generating at least two intermediate images. As a further example, the storage device 150 may store a target image of the subject generated based on the imaging data. In some embodiments, the storage device 150 may store data and/or instructions that the processing device 140 may execute or use to perform exemplary methods described in the present disclosure. For example, the storage device 150 may store instructions that the processing device 140 may execute to process the imaging data acquired by the imaging device 110. In some embodiments, the storage device 150 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components (e.g., the imaging device 110, the processing device 140, the terminal device 130) of the imaging system 100. One or more components of the imaging system 100 may access the data or instructions stored in the storage device 150 via the network 120. In some embodiments, the storage device 150 may be directly connected to or communicate with one or more components (e.g., the imaging device 110, the processing device 140, the terminal device 130) of the Imaging system 100. In some embodiments, the storage device 150 may be part of the processing device 140.

In some embodiments, the imaging system 100 may further include one or more power supplies (not shown in FIG. 1) connected to one or more components (e.g., the imaging device 110, the processing device 140, the terminal device 130, the storage device 150) of the imaging system 100.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 2:
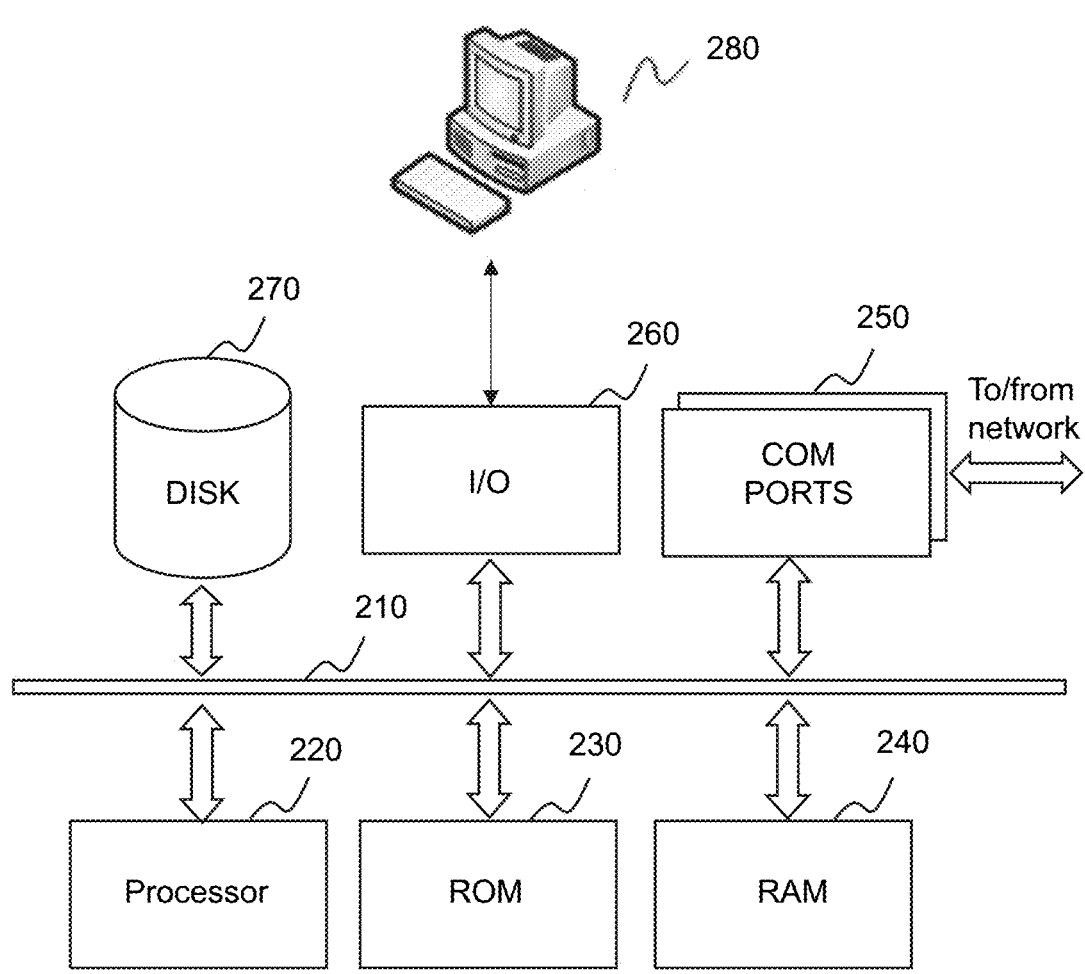
FIG. 2 is a schematic diagram illustrating exemplary hardware and/or software components of an exemplary computing device according to some embodiments of the present disclosure.

FIG. 2 is a schematic diagram illustrating exemplary hardware and/or software components of an exemplary computing device according to some embodiments of the present disclosure. In some embodiments, the processing device 140 may be implemented on the computing device 200. As illustrated in FIG. 2, the computing device 200 may include a data bus 210, a processor 220, a read only memory (ROM) 230, a random access memory (RAM) 240, a communication port 250, an input/output (I/O) 260, a disk 270, and a user interface device 280.

The data bus 210 may be configured to implement data communications among components of the computing device 200. In some embodiments, hardware in the computing device 200 may transmit data via the data bus 210. For example, the processor 220 may send data to a storage or other hardware such as the I/O 260 via the data bus 210. In some embodiments, the data bus 210 may include an industry standard (ISA) bus, an extended industry standard (EISA) bus, a video electronic standard (VESA) bus, an external component interconnect standard (PCI) bus, or the like.

The processor 220 may execute computer instructions (program code) and perform functions of the processing device 140 in accordance with techniques described herein. The computer instructions may include routines, programs, objects, components, signals, data structures, procedures, modules, and functions, which perform particular functions described herein. For example, the processor 220 may obtain imaging data of a subject from the imaging device 110 and generate a first image based on the imaging data. In some embodiments, the processor 220 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration purposes, only one processor is described in the computing device 200. However, it should be noted that the computing device 200 in the present disclosure may also include multiple processors, and thus operations of a method that are performed by one processor as described in the present disclosure may also be jointly or separately performed by the multiple processors. For example, if in the present disclosure the processor of the computing device 200 executes both operations A and B, it should be understood that operations A and step B may also be performed by two different processors jointly or separately in the computing device 200 (e.g., a first processor executes operation A and a second processor executes operation B, or the first and second processors jointly execute operations A and B).

The ROM 230 and/or the RAM 240 may store data/information obtained from the imaging device 110, the terminal device 130, the storage device 150, or any other component of the imaging system 100. In some embodiments, the RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the ROM 230 and/or the RAM 240 may store one or more programs and/or instructions to perform exemplary methods described in the present disclosure. For example, the ROM 230 and/or the RAM 240 may store a program for the processing device 140 for generating a target image based on imaging data of a subject.

The communication port 250 may be connected to a network (e.g., the network 120) to facilitate data communications. The communication port 250 may establish connections between the processing device 140 and the imaging device 110, the terminal device 130, the storage device 150, or any other component of the imaging system 100. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 250 may be a standardized communication port, such as RS232, RS485, etc. In some embodiments, the communication port 250 may be a specially designed communication port. For example, the communication port 250 may be designed in accordance with the digital imaging and communications in medicine (DICOM) protocol.

The I/O 260 may input or output signals, data, or information. In some embodiments, the I/O 260 may enable user interaction with the processing device 140. In some embodiments, the I/O 260 may include an input device and an output device. Exemplary input devices may include a keyboard, a mouse, a touch screen, a microphone, a trackball, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

Merely by way of example, a user (e.g., an operator) may input data related to a subject (e.g., a patient) that is being/to be imaged/scanned through the I/O 260. The data related to the subject may include identification information (e.g., a name, an age, a gender, a height, a weight, a medical history, contract information, a physical examination result). The user may also input parameters needed for the operation of the imaging device 110, such as image contrast and/or ratio, a region of interest (ROI), slice thickness, an imaging type, a scan type, a sampling type, or the like, or any combination thereof. The I/O 260 may also display images generated based on imaging data (e.g., a first image generated based on imaging data of a subject, at least two intermediate images generated based on the first image, a target image generated based on the at least two intermediate images).

The computing device 200 may also include different forms of program storage units and data storage units. For example, the disk 270 may store various data files used for computer processing and/or communication, and program instructions executed by the processor 220. In some embodiments, the disk 270 may include a mechanical hard disk (HDD), a solid-state hard disk (SSD), or a hybrid hard disk (HHD).

The user interface device 280 may implement interaction and information exchange between the computing device 200 and the user.

Figure 3:
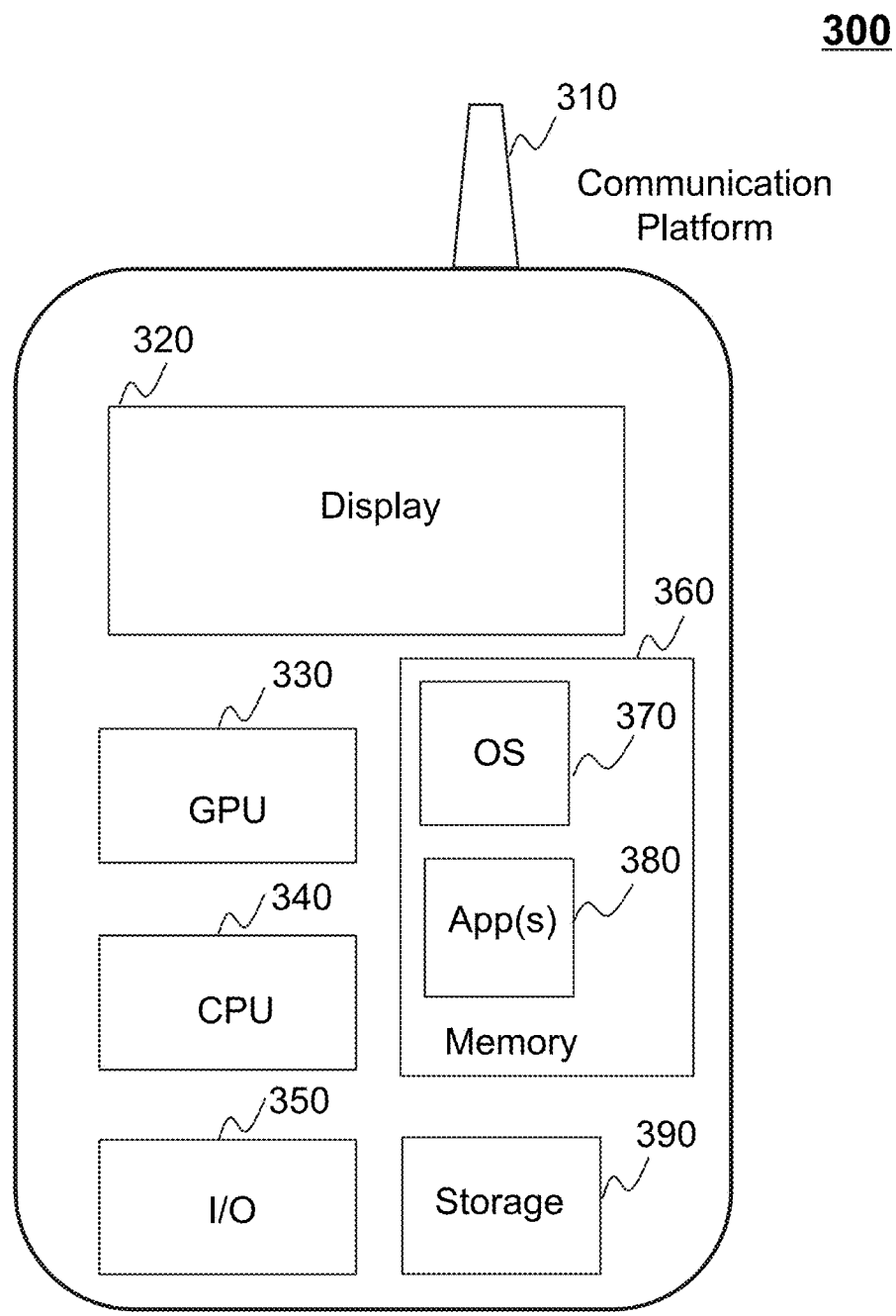
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device according to some embodiments of the present disclosure. In some embodiments, the terminal device 130 may be implemented on the mobile device 300. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300.

In some embodiments, a mobile operating system 370 (e.g., iOS, Android, Windows Phone) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the imaging system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to the blood pressure monitoring as described herein. A computer with user interface elements may be used to implement a personal computer (PC) or another type of work station or terminal device, although a computer may also act as a server if appropriately programmed. The image processing systems and methods may be implemented in the imaging system 100. It is believed that those skilled in the art are familiar with the structure, programming and general operation of such computer equipment and as a result the drawings should be self-explanatory.

Figure 4:
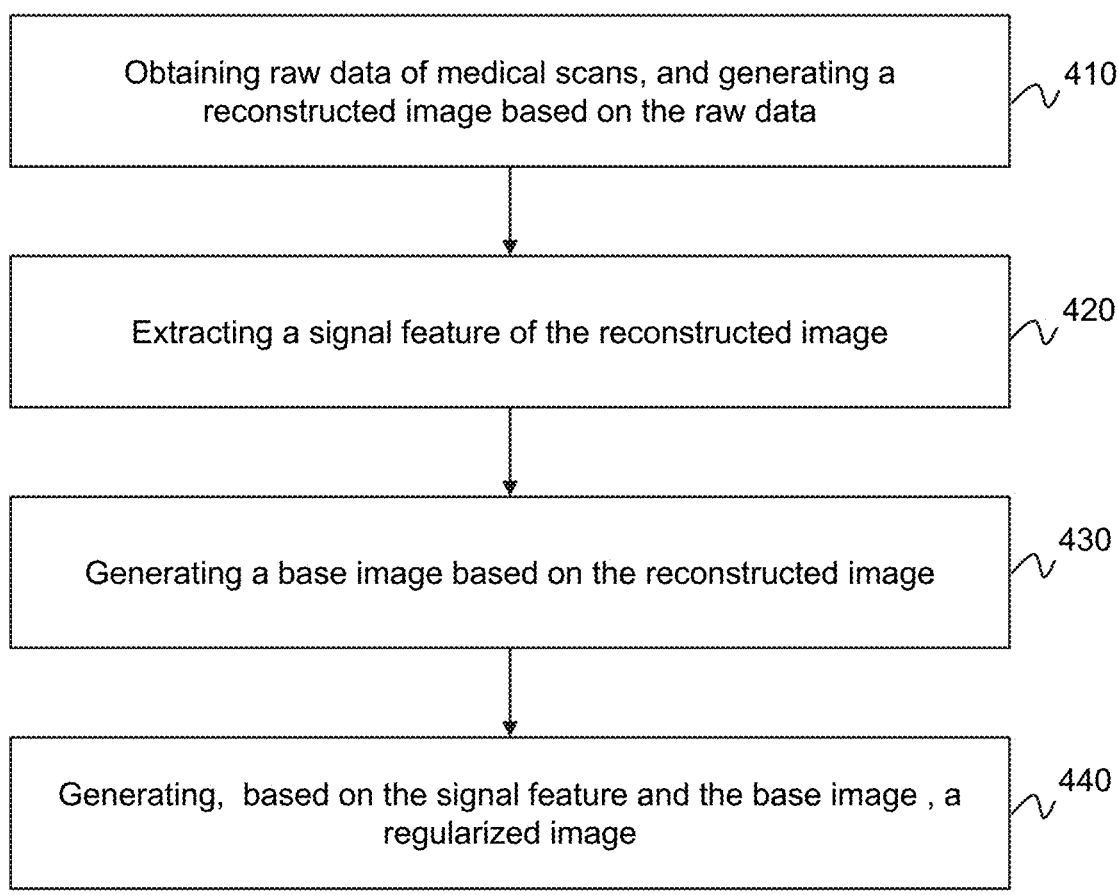
FIG. 4 is a flowchart illustrating an exemplary process for reconstructing a regularized image according to some embodiments of the present disclosure.

FIG. 4 is a flowchart illustrating an exemplary process for reconstructing a regularized image according to some embodiments of the present disclosure. In some embodiments, the process 400 may be implemented by an imaging system (e.g., the imaging system 100). In some embodiments, the imaging system may be implemented by software and/or hardware. In some embodiments, at least part of process 400 may be performed by the processing device 140 (implemented in, for example, the computing device 200 shown in FIG. 2). For example, the process 400 may be stored in a storage device (e.g., the storage device 150, the ROM 230, the RAM 240, the storage 390) in the form of instructions (e.g., an application), and invoked and/or executed by the processing device 140 (e.g., the processor 220 illustrated in FIG. 2, the CPU 340 illustrated in FIG. 3, one or more modules illustrated in FIG. 9 or FIG. 10). The operations of the illustrated process presented below are intended to be illustrative. In some embodiments, the process 400 may be accomplished with one or more additional operations not described, and/or without one or more of the operations discussed. Additionally, the order in which the operations of the process 400 as illustrated in FIG. 4 and described below is not intended to be limiting.

In 410, raw data of medical scans (also referred to as "imaging data") may be obtained, and a reconstructed image (also referred to as "first image") may be generated based on the raw data. In some embodiments, the processing device 140 (e.g., the data processing module 910 illustrated in FIG. 9 or FIG. 10) may perform operation 410.

In some embodiments, the raw data may be acquired based on an interaction between a subject (e.g., a human body) and a medium provided or detected by an imaging device (e.g., the imaging device 110 illustrated in FIG. 1) during a medical scanning process. In some embodiments, the subject may include a patient, a man-made object, etc. In some embodiments, the subject may include a specific portion, organ, and/or tissue of a patient. For example, the subject may include a head, a brain, a neck, a body, a shoulder, an arm, a thorax, a cardiac, a stomach, a blood vessel, a soft tissue, a knee, feet, or the like, or any combination thereof. Exemplary mediums may include an X-ray beam, an electromagnetic field, an ultrasonic wave, a radioactive tracer, or the like, or any combination thereof. Exemplary imaging devices may include an MR scanning device, a CT scanning device, an X-ray scanning device, an ultrasound scanning device, a PET scanning device, a DR scanning device, or the like, or any combination thereof.

In some embodiments, the raw data may be obtained from the imaging device directly. For example, during a medical scanning process of the imaging device 110, the subject may be placed on the scanning table 114 and scanned in the detection region 113 by the imaging device 110. The detector assembly 112 may detect radiation events (e.g., gamma photons) emitted from the detection region 113 and generate electrical signals. The electronic module 115 may process the electrical signals and generate the raw data. Further, the processing device 140 may obtain the raw data from the electronic module 115 directly. In some embodiments, the raw data may be retrieved from a storage device (e.g., the storage device 150) disclosed elsewhere in the present disclosure. For example, a database may be configured in the storage device 150 for storing the raw data. The raw data generated by the imaging device 110 may be transferred to the storage device 150 and stored in the database. The processing device 140 may obtain the raw data from the database. In some embodiments, the raw data may be in the form of an image matrix.

In some embodiments, to generate the reconstructed image, the processing device 140 may perform a reconstruction operation on the raw data. Exemplary reconstruction operations may include a projection operation, a transformation operation, or the like, or any combination thereof.

In some embodiments, the processing device 140 may generate the reconstructed image by performing the projection operation based on the raw data. For example, for the raw data acquired in a PET imaging system or a CT imaging system, the processing device 140 may generate the reconstructed image by performing the projection operation. In some embodiments, the projection operation may include forward projection and back projection. For example, the processing device 140 may determine an initial image. Further, the processing device 140 may obtain forward projection data (or a forward projection image) by performing forward projection on the initial image. Further, the processing device 140 may obtain the reconstructed image by performing back projection based on the forward projection data and the raw data. In the projection operation, the raw data may be used for generating the reconstructed image.

In some embodiments, the projection operation may be performed based on an iterative reconstruction algorithm. For example, the processing device 140 may perform forward projection and back projection iteratively. In each iteration, the processing device 140 may determine whether a termination condition is satisfied in the current iteration. Exemplary termination conditions may include that a certain count of iterations has been performed, a difference between the reconstructed images in the current iteration and in the previous iteration is less than a certain threshold, etc. The certain count may be a default value of the imaging system 100, manually set by a user or an operator, or determined by the processing device 140 according to an actual need. If the termination condition is satisfied in the current iteration, the processing device 140 may designate the reconstructed image in the current iteration as a target reconstructed image.

Merely by way of example, in an image reconstruction of PET imaging data, a forward projection operation may be performed according to Equation (1) below:

$$P_j = \Sigma_i M_{ij} F_i^n, \quad (1)$$

where $F_i^n$ denotes the initial image in the $n^{th}$ iteration, $P_j$ denotes forward projection data of the initial image $F_i^n$ along a response line j, and $M_{ij}$ denotes a contribution of a pixel i of the initial image $F_i^n$ to the response line j. In some embodiments, in a first iteration of the projection operation, each pixel of the initial image may be assigned an initial value (e.g., 1). In each subsequent iteration, back projection data generated in the previous iteration may be used as the initial image.

A back projection operation may be performed according to Equation (2) below:

$$\tilde{F}_i^{n+1} = \frac{F_i^n}{\Sigma_j M_{ij}} \Sigma_j M_{ij} \frac{y_j}{P_j}, \quad (2)$$

where $\tilde{F}_i^{n+1}$ denotes back projection data (or reconstructed images in the current iteration), and $y_j$ denotes the raw data acquired by the imaging device on the response line j.

In some embodiments, the processing device 140 may generate the reconstructed image by performing the transformation operation based on the raw data. For example, for the raw data acquired in an MR imaging system, the processing device 140 may generate the reconstructed image by performing the transformation operation. In some embodiments, the transformation operation may include a transformation operation and an inverse transformation operation. For example, the processing device 140 may determine an initial image. Further, the processing device 140 may obtain a sampling image in a k-space by performing a transformation operation on the initial image. Further, the processing device 140 may obtain the reconstructed image by performing an inverse transformation operation based on the sampling data and the raw data. In the transformation operation, the raw data may be used for generating the reconstructed image.

In some embodiments, the transformation operation may be performed based on an iterative reconstruction algorithm. For example, the processing device 140 may perform the transformation operation and the inverse transformation operation iteratively. In each iteration, the processing device 140 may determine whether a termination condition is satisfied in the current iteration. If the termination condition is satisfied in the current iteration, the processing device 140 may designate the reconstructed image in the current iteration as a target reconstructed image.

Merely by way of example, the transformation operation may be performed based on a Fourier transform algorithm according to Equation (3) below:

$$Q_i = F(F^n), \quad (3)$$

where $F^n$ denotes the initial image in the $n^{th}$ iteration, and $Q_i$ denotes a transformation image of the initial image $F^n$. In some embodiments, in a first iteration of the transformation operation, each pixel of the initial image may be assigned an initial value (e.g., 1). In each subsequent iteration, an inverse transformation image generated in the previous iteration may be used as the initial image.

The inverse transformation step may be performed based on an inverse Fourier transform algorithm according to Equation (4) below:

$$\tilde{F}^{n+1} = F^{-1}(\tilde{Q}_j), \quad (4)$$

where $\tilde{F}^{n+1}$ denotes an inverse transformation image, $F^{n-1}$ denotes a Fourier transform operation, and may be generated according to Equation (5) below:

$$\tilde{Q}_j = \begin{cases} y_j, & j \in J \\ Q_j, & \text{others} \end{cases}, \quad (5)$$

where $y_j$ denotes the raw data acquired by the imaging device on the response line j, J denotes data points in the k space, $\tilde{Q}_j$ denotes the sampling image generated based on the raw data $y_j$ and the transformation image $Q_j$.

According to the reconstruction operation, the raw data may be used for generating the reconstructed image by transformation or projection. In such cases, feature information may be retained in the reconstructed image. Exemplary feature information may include gradient information, pixel information, grayscale information, or the like. In some embodiments, the reconstructed image may also include noise. For example, a relatively low detected count used by the imaging device may cause noise in the raw data. The noise in the raw data so acquired may be preserved and/or reflected in the reconstructed image generated based on the raw data. As used herein, the detected count, also referred to as detected count rate, may refer to a rate of counts of radiation events detection by a detector (e.g., the detector assembly 112) per unit time (e.g., per minute, per second, etc.).

In 420, a signal feature (also referred to as "feature information") of the reconstructed image may be extracted. In some embodiments, the signal feature may be expressed in the form of an image (or a matrix), which may also be referred to as a first intermediate image. In some embodiments, the processing device 140 (e.g., the feature extraction module 920 illustrated in FIG. 9 or FIG. 10) may perform operation 420.

In some embodiments, the signal feature may be described in terms of, e.g., the gradient information, the pixel information, the grayscale information, or the like, or a combination thereof. The gradient information may refer to a gradient of pixel values (or voxel values) of the reconstructed image along a specific direction. In some embodiments, the gradient information may be used to reflect boundary information relating to the subject (e.g., a specific portion, an organ, and/or a tissue of a patient). In some embodiments, the gradient information may be expressed in the form of a matrix. The matrix may include a row matrix, a column matrix, an asymmetric matrix, a diagonal matrix, a decomposed matrix, or the like, or any combination thereof. Merely by way of example, the reconstructed image may also be expressed in the form of a matrix. The matrix corresponding to the gradient information may have a same dimension (e.g., 256×256, 64×64, etc.) as the matrix corresponding to the reconstructed image. The pixel information may be used to reflect a distribution of pixels (or voxels) in terms of, e.g., a pixel/voxel value, a location of each pixel, or the like, or a combination thereof, of the reconstructed image. The grayscale information may be used to reflect luminance (or brightness) information of pixels in the reconstructed image (e.g., a grayscale image).

In some embodiments, to extract the signal feature of the reconstructed image, the processing device 140 may generate a feature map based on the reconstructed image. Further, the processing device 140 may determine the signal feature of the reconstructed image based on the feature map. In some embodiments, to generate the feature map, the processing device 140 may obtain a second-order differential value in the three-dimensional space and a pixel mean value of the reconstructed image. Further, the processing device 140 may generate the feature map based on the second-order differential value in the three-dimensional space and the pixel mean value of the reconstructed image. In some embodiments, the second-order differential operation may have a sharpening effect such that the boundary information in the reconstructed image may be improved, e.g., the location of the boundary being more accurate, the contrast between the boundary and its vicinity being enhanced. That is, the second-order differential value may be used to reflect the gradient information. In some embodiments, the grayscale information may correspond to the pixel information. For example, the reconstructed image may include a grayscale image. In the grayscale image, the grayscale information may be the same as or similar to the pixel information. That is, the pixel mean value of the reconstructed image may be used to reflect the pixel information and the grayscale information. In such cases, the feature map generated based on the second-order differential value in the three-dimensional space and the pixel mean value of the reconstructed image may include the signal feature of the reconstructed image. Optionally or additionally, assuming that the reconstructed image is a 2D image, the processing device 140 may also generate the feature map based on a first-order differential value in the two-dimensional space and the pixel mean value of the reconstructed image. In some embodiments, after generating the feature map, the processing device 140 may determine the signal feature from the feature map based on a feature extraction algorithm (e.g., a signal extraction algorithm).

In 430, a base image (also referred to as "second intermediate image") may be generated based on the reconstructed image. In some embodiments, the processing device 140 (e.g., the feature extraction module 920 illustrated in FIG. 9 or FIG. 10) may perform operation 430.

In some embodiments, to generate the base image, the reconstructed image may be input into a neural network (also referred to as "second machine learning model"), and an output of the neural network may be obtained as the base image. As used herein, the neural network may be configured to process signals and/or noise in the reconstructed image, which may reduce or remove the noise in the reconstructed image and/or enhance the signal feature in the reconstructed image, thereby improving a signal-to-noise ratio of the base image. Exemplary neural networks may include a convolutional neural network (CNN), a generative adversarial network (GAN), a neural network derived from the CNN and/or GAN, or the like, or any combination thereof.

Merely by way of example, the base image may be generated according to Equation (6) below:

$$B=NN(\tilde{F}^{n+1}), \quad (6)$$

where $\tilde{F}^{n+1}$ denotes the reconstructed image, and NN denotes a neural network. An exemplary process for generating a base image using a neural network may be found elsewhere in the present disclosure. See, e.g., FIG. 5, FIG. 6, and the descriptions thereof.

In some embodiments, the neural network used in the generation of the base image based on the reconstructed image may be trained offline before the generation of the base image. In some embodiments, the neural network may be trained online concurrently with the generation of the base image. An exemplary process for concurrent online training of the neural network and determination of a base image, both based on a reconstructed image, may be found in FIG. 6. In some embodiments, the training (regardless of online or offline training) of a neural network may be performed according to the process exemplified in FIG. 11. The difference between an online training and an offline training of a neural network may include whether the training data set used in the training includes images of a sample subject, when the training is performed (at the time of its application or in advance), etc.

In some embodiments, the base image may be generated by performing a filtering operation on the reconstructed image. For example, to generate the base image, the processing device 140 may perform, based on a filtering algorithm, the filtering operation on the reconstructed image. The filtering algorithm may be used to reduce or remove the noise in the reconstructed image. Exemplary filtering algorithms may include a Gaussian filtering algorithm, a non-local mean (NLM) filtering algorithm, a block-matching and 3D (BM3D) filtering algorithm, or the like, or any combination thereof.

In 440, a regularized image (also referred to as "target image") may be generated based on the signal feature and the base image. In some embodiments, the processing device 140 (e.g., the image reconstruction module 930 illustrated in FIG. 9 or FIG. 10) may perform operation 440.

In some embodiments, the regularized image may be generated by fusing the signal feature and the base image. For example, the processing device 140 may perform a weighted fusion by assigning different weights to the base image and the signal feature. Merely by way of example, the processing device 140 may determine a first weight for the signal feature, and determine a second weight for the base image. Further, the processing device 140 may generate the regularized image by combining, based on the first weight and the second weight, the signal feature and the base image.

In some embodiments, the first weight may be larger than the second weight. The signal feature and the base image may be expressed in the form of matrices of a same dimension. Elements in a same matrix position of the two matrices, or referred to as corresponding elements, may correspond to a same position of a subject. Correspondingly, the first weight and the second weight may also be expressed in the form of matrices of the same dimension as the signal feature and the base image. At least a portion of elements of the first weight may be larger than the corresponding elements of the second weight. For example, since the feature information is retained in the signal feature, each element in the first weight may be larger than a corresponding element in the second weight. As another example, since the boundary information in the reconstructed image is retained and/or enhanced in the gradient information, the signal feature may be mainly used to reflect the boundary information. Accordingly, elements in the first weight corresponding to the boundary information may be larger than corresponding elements in the second weight. And other elements in the first weight not corresponding to the boundary information may be smaller than corresponding elements in the second weight. In such cases, the boundary information may be enhanced in the regularized image, and other portions of the regularized image may be the same as the corresponding portions of the base image. Then the signal feature may be retained in the regularized image, and a signal-to-noise ratio of the regularized image may be improved.

In some embodiments, the regularized image may be updated according to an iterative operation including one or more iterations. For example, in the reconstruction operation of a current iteration, the regularized image obtained in a previous iteration may be used as the initial image for generating an updated reconstructed image (e.g., by performing a projection operation or a transformation operation). Further, the updated reconstructed image generated based on the regularized image in the previous iteration and the raw data may be used to generate an updated base image and/or extract an updated signal feature. Further, the updated base image and the updated signal feature may be used to generate the regularized image in the current iteration. In such cases, the regularized image may be generated or updated iteratively until a termination condition is satisfied. Exemplary termination conditions may include a difference (e.g., a difference of corresponding pixel values) between the regularized images generated the previous iteration and the current iteration is in a certain range, a certain count of iterations has been performed, or the like, or any combination thereof. In some embodiments, as discussed in connection with operation 430 and FIG. 6, the neural network may be trained online concurrently with the generation of the base image. Accordingly, the neural network may be trained iteratively during the iterative operation for updating the regularized image. For example, the neural network may be trained in each iteration included in the iterative operation for updating the regularized image. In the iteration, the reconstructed image generated based on the regularized image in the previous iteration may be used as the target for training the neural network. As a further example, the neural network may be trained in certain iterations included in the iterative operation for updating the regularized image. Merely by way of example, the regularized images generated in previous iterations may have lower quality (e.g., including less signal feature and/or higher noise) than the regularized images generated in later iterations. In such cases, the neural network may be trained in such later iterations. For instance, the neural network may be trained after a certain count of iterations (e.g., 4 iterations, 5 iterations, 6 iterations, etc.) are performed.

As another example, the feature map may be generated according to an iterative operation. In some embodiments, the extraction of the signal feature may include three operations including generating a feature map based on the reconstructed image, extracting the signal feature from the feature map, and generating the regularized image based on the signal feature and the base image. In the extraction of the signal feature of the current iteration, the regularized image obtained in a previous iteration may be used as the feature map. The signal feature may be extracted from the regularized image obtained in the previous iteration. Further, the signal feature extracted from the regularized image obtained in the previous iteration and the base image may be used to generate the regularized image in the current iteration. In such cases, the feature map may be generated iteratively until a termination condition is satisfied. Exemplary termination conditions may include a certain count of iterations have been performed. According to the iterative operation, the regularized image obtained in a previous iteration may be used as the feature map for extracting the signal feature. In such cases, more complete signal feature may be retained in the regularized image generated after the iterative operation.

According to the method for reconstructing the regularized image illustrated in the process 400, the reconstructed image may be generated based on the raw data of medical scans such that the feature information may be retained in the reconstructed image. Further, the reconstructed image may be processed in two or more operations. The two or more operations may include extracting the signal feature and generating the base image. Further, the signal feature and the base image may be combined to generate the regularized image. While in a conventional method for reconstructing a regularized image, a neural network may be used to regularize an image to generate a reconstructed image directly. According to such a conventional method, multiple aspects of image processing to generate a target image based on raw data or a reconstructed image (that is generated by image reconstruction or transformation performed on the raw data), e.g., boundary information, noise reduction, etc., may need to be taken care of by a single neural network. Accordingly, such a neural network may involve more complicated convolution calculations and requires more training samples in the training thereof. Compared with such a conventional method, the neural network in the present disclosure may be used to reduce the noise in the reconstructed image, which may involve simpler convolution calculations and takes fewer training samples. Additionally, the method according to embodiments of the present disclosure may generate an accurate regularized image with lower noise.

It should be noted that the method for reconstructing a regularized image illustrated in the process 400 may be executed on a console of a medical device (e.g., the imaging device 110), or may be executed on a post-processing workstation of the medical device, on the terminal device 130 that communicates with the medical device, or on the computing device 200 that implements a processing engine, according to actual application needs.

It should be noted that the above description of the process 400 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the transformation operation may be performed based on one or more transform algorithms other than a Fourier transform algorithm. Accordingly, the inverse transformation operation may be performed based on one or more inverse transform algorithms other than an inverse Fourier transform algorithm. As another example, the signal feature may also be extracted based on an extraction neural network (also referred to as "first machine learning model"). As a further example, the reconstruction operation in operation 410 may also be performed according to other reconstruction techniques, such as an algebraic reconstruction technique (ART), a simultaneous algebraic reconstruction technique (SART), a penalty weighted least squares (PWLS) technique, or the like, or any combination thereof.

Figure 5:
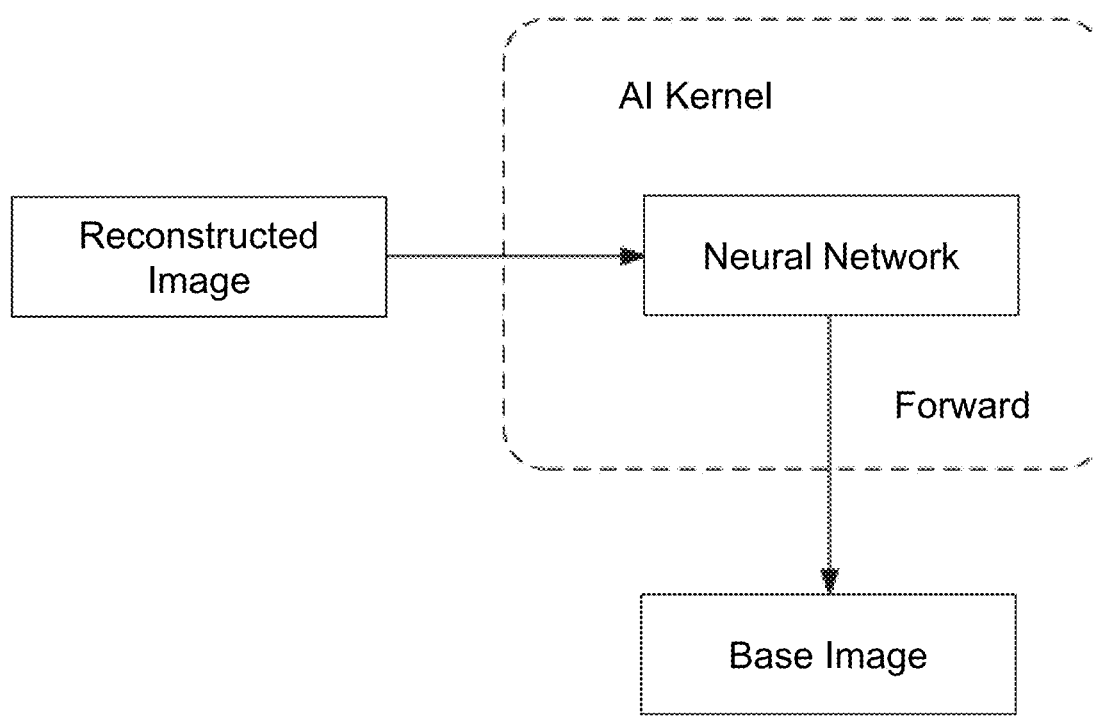
FIG. 5 is a schematic diagram illustrating an exemplary process for generating a base image using a neural network according to some embodiments of the present disclosure.

FIG. 5 is a schematic diagram illustrating an exemplary process for generating a base image using a neural network according to some embodiments of the present disclosure. As illustrated in FIG. 5, the reconstructed image may be input into an artificial intelligence (AI) kernel including a trained neural network. The trained neural network may be caused to perform a forward operation on the reconstructed image. Further, the base image may be output by the trained neural network.

Figure 6:
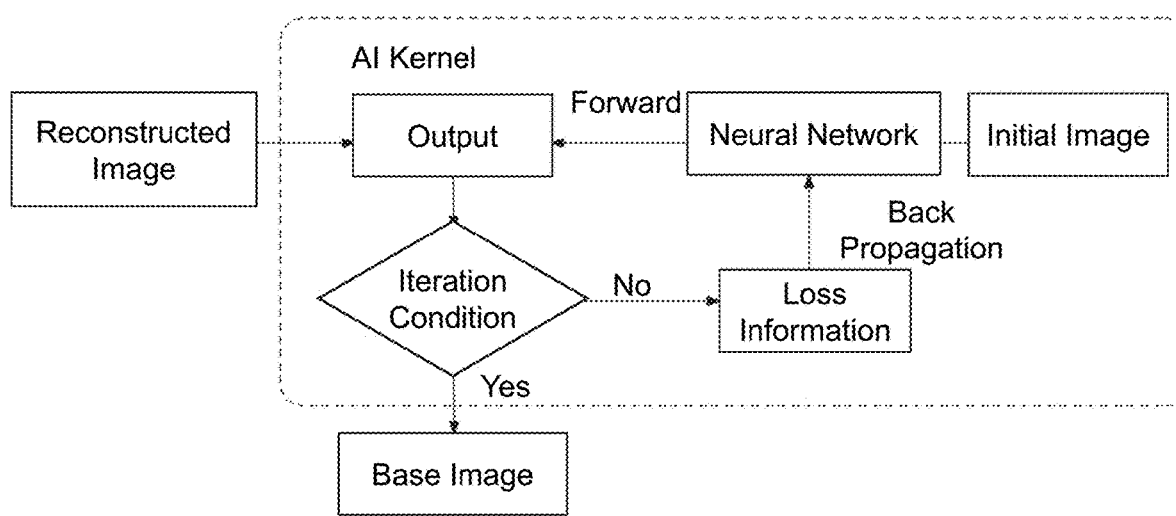
FIG. 6 is a schematic diagram illustrating an exemplary process for concurrent online training of the neural network and determination of a base image according to some embodiments of the present disclosure.

FIG. 6 is a schematic diagram illustrating an exemplary process for concurrent online training of the neural network and determination of a base image according to some embodiments of the present disclosure.

As illustrated in FIG. 6, to generate the base image, the reconstructed image may be input into a preliminary neural network, and a third image may be generated by the preliminary neural network. The preliminary neural network may not be trained before the determination of the base image. For example, when an AI kernel including the preliminary neural network is invoked, the preliminary neural network may be initialized. An initial image obtained randomly may be used as an input, and the reconstructed image may be used as a target for training the preliminary neural network. The initial image may be obtained by the preliminary neural network randomly. During the training process, a forward operation may be performed by the preliminary neural network to generate an output (i.e., the third image). Further, loss information configured to assess a difference between the reconstructed image and the third image may be obtained. Parameters of the preliminary neural network may be updated based on the loss information iteratively according to a backpropagation algorithm until a termination condition is satisfied. Further, the third image generated using the updated neural network may be designated as the based image. That is, the neural network may be trained when it is used to generate the base image. During the training process, the neural network may output the third image by performing a forward operation based on the reconstructed image. The loss information between the reconstructed image and the third image may be used to update the neural network iteratively according to a backpropagation algorithm. Further, when the termination condition is satisfied, the third image currently output by the neural network may be designated as the base image. Exemplary termination conditions may include the signal-to-noise ratio of the third image is higher than or equal to a threshold, or a certain count of iterations has been performed, or the like, or a combination thereof.

According to the training process during the generation of the base image, the neural network may be trained online when it is used to generate the base image. During the training process, the reconstructed image may be used for training the neural network. In such cases, the neural network may be trained without preparing a training data set beforehand, thereby reducing the reliance of the training process on the availability of training data without compromising the accuracy of the base image determined concurrently with the online training of the neural network.

Figure 7A:
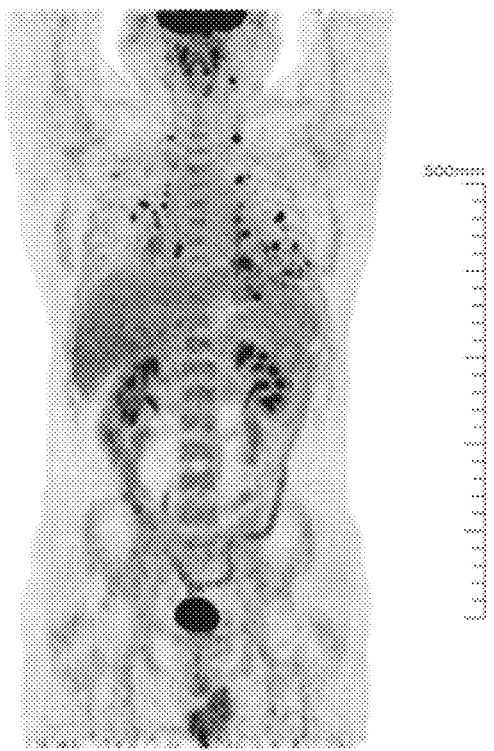
FIGS. 7a and 7b provide exemplary images of a subject generated using a conventional method and a method according to some embodiments of the present disclosure, respectively.
Figure 7B:
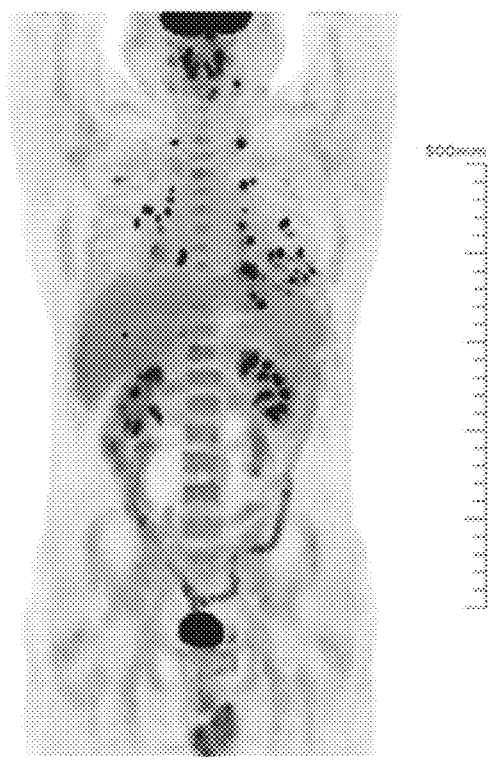
Figure 8A:
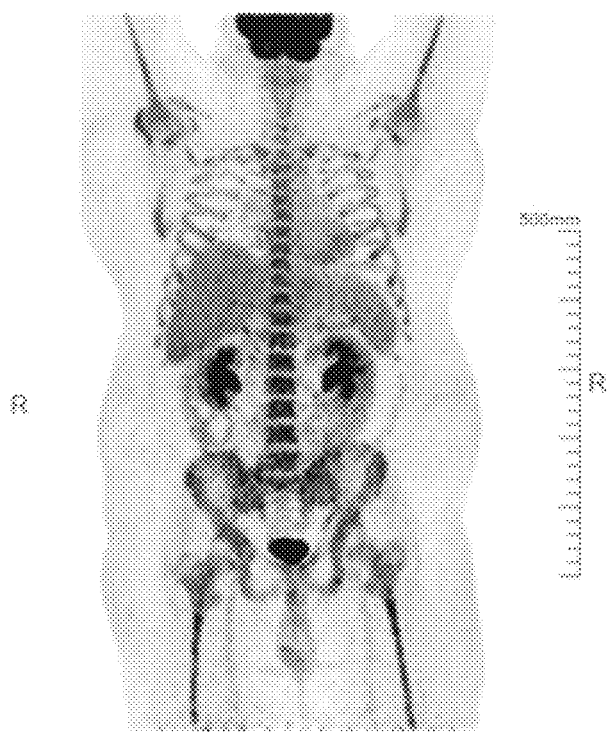
FIGS. 8a and 8b provide exemplary images of a subject generated using a conventional method and a method according to some embodiments of the present disclosure, respectively.
Figure 8B:
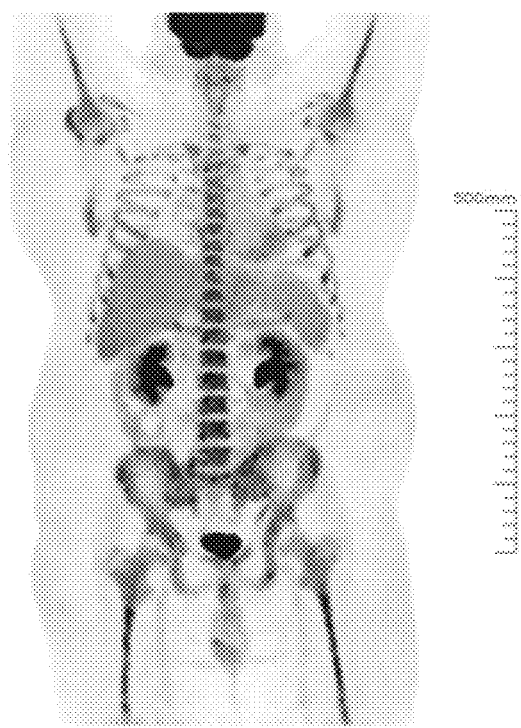

FIGS. 7a and 7b provide exemplary images of a subject generated using a conventional method and a method according to some embodiments of the present disclosure, respectively. FIGS. 8a and 8b provide exemplary images of another subject generated using a conventional method and a method according to some embodiments of the present disclosure, respectively. The images illustrated in FIG. 7a and FIG. 8a were generated according to an ordinary Poisson ordered subset expectation maximization (OP-OSEM) algorithm in the conventional method. The images (also referred to as "regularized images") illustrated in FIG. 7b and FIG. 8b were generated according to the method as described in some embodiments of the present disclosure. As shown in FIGS. 7a-8b, the images generated according to the method as described in some embodiments of the present disclosure provide better boundary information (e.g., outlines of a torso, bones, lungs, etc. of the subject) and a higher signal-to-noise ratio than the images generated according to the OSEM algorithm.

Figure 9:
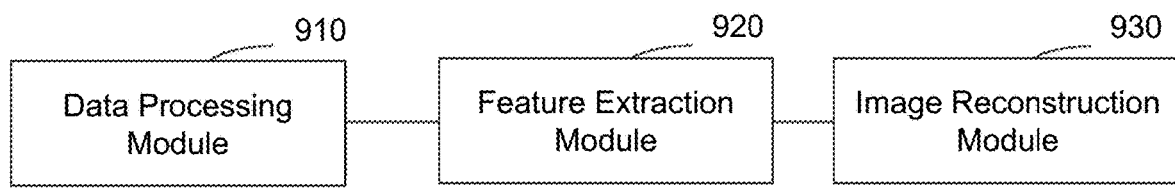
FIG. 9 is a schematic diagram illustrating an exemplary regularized image reconstruction system according to some embodiments of the present disclosure.

FIG. 9 is a schematic diagram illustrating an exemplary regularized image reconstruction system according to some embodiments of the present disclosure. In some embodiments, the regularized image reconstruction system may be implemented by means of software and/or hardware. For example, the regularized image reconstruction system may be implemented on various components (e.g., the computing device 200 as illustrated in FIG. 2, the mobile device 300 as illustrated in FIG. 3). As shown in FIG. 9, the regularized image reconstruction system may include a data processing module 910, a feature extraction module 920, and an image reconstruction module 930.

The data processing module 910 may be configured to obtain raw data of medical scans, and generate a reconstructed image based on the raw data. In some embodiments, the data processing module 910 may be configured to obtain the raw data from the imaging device directly. In some embodiments, the data processing module 910 may be configured to retrieve the raw data from a storage device (e.g., the storage device 150) disclosed elsewhere in the present disclosure.

In some embodiments, to generate the reconstructed image, the data processing module 910 may be configured to perform a reconstruction operation on the raw data. Exemplary reconstruction operations may include a projection operation, a transformation operation, or the like, or any combination thereof.

The feature extraction module 920 may be configured to extract a signal feature of the reconstructed image. In some embodiments, the signal feature may be described in terms of, e.g., gradient information, pixel information, grayscale information, or the like, or a combination thereof. In some embodiments, to extract the signal feature of the reconstructed image, the feature extraction module 920 may be configured to generate a feature map based on the reconstructed image. Further, the feature extraction module 920 may be configured to determine the signal feature of the reconstructed image based on the feature map. For example, after generating the feature map, the feature extraction module 920 may determine the signal feature from the feature map based on a feature extraction algorithm (e.g., a signal extraction algorithm). In some embodiments, to generate the feature map, the feature extraction module 920 may obtain a second-order differential value in the three-dimensional space and a pixel mean value of the reconstructed image. Further, the feature extraction module 920 may generate the feature map based on the second-order differential value in the three-dimensional space and the pixel mean value of the reconstructed image. In some embodiments, to extract the signal feature of the reconstructed image, the feature extraction module 920 may be configured to determine the feature information of the reconstructed image based on a first machine learning model.

The feature extraction module 920 may be further configured to generate a base image based on the reconstructed image. In some embodiments, the feature extraction module 920 may be configured to generate the base image by performing a filtering operation on the reconstructed image. In some embodiments, to generate the base image, the feature extraction module 920 may be configured to input the reconstructed image into a neural network. The neural network may be configured to process signals and/or noise in the reconstructed image. In some embodiments, to generate the base image, the feature extraction module 920 may be configured to input the reconstructed image into a preliminary neural network, and obtain a third image generated by the preliminary neural network. Further, the feature extraction module 920 may be configured to obtain loss information configured to assess a difference between the reconstructed image and the third image, and update parameters of the preliminary neural network based on the loss information iteratively until a termination condition is satisfied. Further, the third image generated using the updated neural network may be designated as the based image.

The image reconstruction module 930 may be configured to generate a regularized image based on the signal feature and the base image. In some embodiments, to generate the regularized image, the image reconstruction module 930 may be configured to perform a weighted fusion by assigning different weights to the base image and the signal feature.

Figure 10:
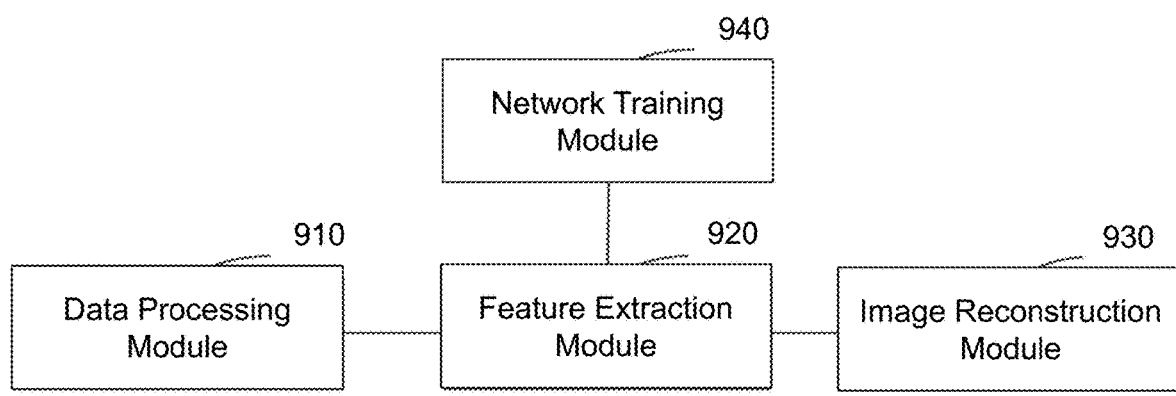
FIG. 10 is a schematic diagram illustrating an exemplary regularized image reconstruction system according to some embodiments of the present disclosure.

FIG. 10 is a schematic diagram illustrating an exemplary regularized image reconstruction system according to some embodiments of the present disclosure. In some embodiments, as illustrated in FIG. 10, the regularized image reconstruction system illustrated in FIG. 9 may further include a network training module 940. The network training module 940 may be configured to generate the neural network according to a model training process. In some embodiments, to generate the neural network, the network training module 940 may obtain a plurality of image pairs of a same or different sample subjects. A sample image pair may include a first image and a second image of a same sample subject. The first image may have a low signal-to-noise ratio, and the second image may have a high signal-to-noise ratio. Further, the network training module 940 may obtain a preliminary neural network. The first image may be used as an input sample for training, and the second image may be used as a target sample for training the preliminary neural network. Further, the network training module 940 may obtain the neural network by training the preliminary neural network based on the plurality sample image pairs.

According to the regularized image reconstruction system, the data processing module 910 is provided to generate the reconstructed image based on the raw data of medical scans such that the feature information may be retained in the reconstructed image. Further, the feature extraction module 920 is provided to process the reconstructed image in two or more operations. The two or more operations may include extracting the signal feature and generating the base image. Further, the image reconstruction module 930 is provided to generate the regularized image by combining the signal feature and the base image. While in a conventional system for reconstructing a regularized image, a neural network may be used to regularize an image to generate a reconstructed image directly. According to such a conventional system, multiple aspects of image processing to generate a target image based on raw data or a reconstructed image (that is generated by image reconstruction or transformation performed on the raw data), e.g., boundary information, noise reduction, etc., may need to be taken care of by a single neural network. Accordingly, such a neural network may involve more complicated convolution calculations and requires more training samples in the training thereof. Compared with such a conventional system, the neural network in the present disclosure may be used to reduce the noise in the reconstructed image, which may involve simpler convolution calculations and takes fewer training samples. Additionally, the regularized image reconstruction system may generate an accurate regularized image with lower noise.

It should be noted that the above descriptions of the regularized image reconstruction system are provided for the purposes of illustration, and not intended to limit the scope of the present disclosure. For persons having ordinary skills in the art, various modifications and changes in the forms and details of the application of the above method and system may occur without departing from the principles of the present disclosure. Merely by way of example, the regularized image reconstruction system may include one or more other modules. However, those variations and modifications also fall within the scope of the present disclosure. For example, the feature extraction module 920 may include a feature extraction unit and a generation unit. The feature extraction unit may be configured to extract the signal feature. The generation unit may be configured to generate the base image.

Figure 11:
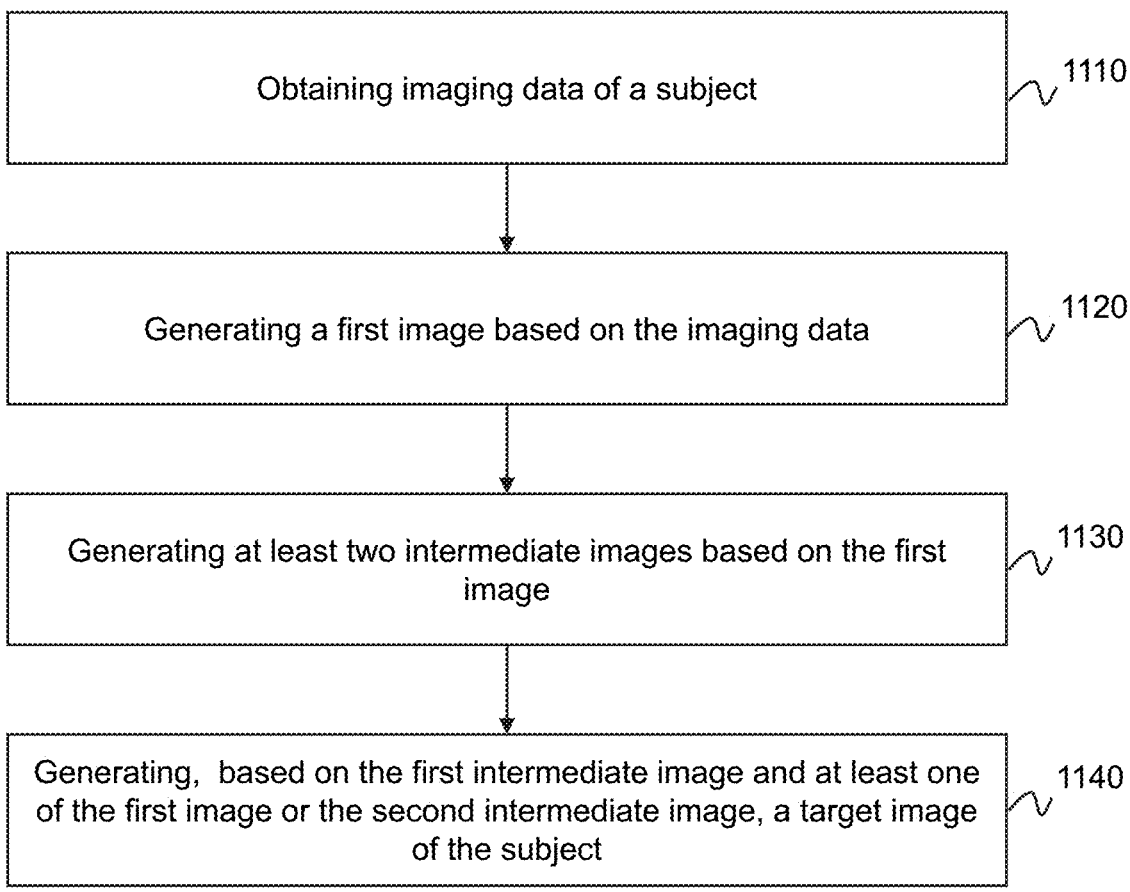
FIG. 11 is a flowchart illustrating an exemplary process for image processing according to some embodiments of the present disclosure.

FIG. 11 is a flowchart illustrating an exemplary process for image processing according to some embodiments of the present disclosure. In some embodiments, the process 1100 may be implemented by an imaging system (e.g., the imaging system 100). In some embodiments, the imaging system may be implemented by software and/or hardware. In some embodiments, at least part of process 1100 may be performed by the processing device 140 (implemented in, for example, the computing device 200 shown in FIG. 2). For example, the process 1100 may be stored in a storage device (e.g., the storage device 150, the ROM 230, the RAM 240, the storage 390) in the form of instructions (e.g., an application), and invoked and/or executed by the processing device 140 (e.g., the processor 220 illustrated in FIG. 2, the CPU 340 illustrated in FIG. 3, one or more modules illustrated in FIG. 9 or FIG. 10). The operations of the illustrated process presented below are intended to be illustrative. In some embodiments, the process 1100 may be accomplished with one or more additional operations not described, and/or without one or more of the operations discussed. Additionally, the order in which the operations of the process 1100 as illustrated in FIG. 11 and described below is not intended to be limiting.

In 1110, the processing device 140 (e.g., the data processing module 910) may obtain imaging data (also referred to as "raw data of medical scans") of a subject.

As described in connection with operation 410, the subject may include a patient, a man-made object, etc. The imaging data may be acquired based on an interaction between the subject (e.g., a human body) and a medium provided or detected by an imaging device (e.g., the imaging device 110 illustrated in FIG. 1) during a medical scanning process.

In some embodiments, the imaging data may be obtained from the imaging device directly. In some embodiments, the imaging data may be retrieved from a storage device (e.g., the storage device 150) disclosed elsewhere in the present disclosure. In some embodiments, the imaging data may be in the form of an image matrix.

In 1120, the processing device 140 (e.g., the data processing module 910) may generate a first image (also referred to as "reconstructed image") based on the imaging data.

In some embodiments, to generate the first image, the processing device 140 may perform, based on the imaging data, a reconstruction operation. Exemplary reconstruction operations may include a projection operation, a transformation operation, or the like, or any combination thereof.

For example, for the imaging data acquired in a PET imaging system or a CT imaging system, the processing device 140 may generate the first image by performing the projection operation. The projection operation may include a forward projection and a back projection. For example, the processing device 140 may determine an initial image. Further, the processing device 140 may obtain forward projection data (or a forward projection image) by performing a forward projection on the initial image. Further, the processing device 140 may obtain the first image by performing a back projection based on the forward projection data and the imaging data.

As another example, for the imaging data acquired in an MR imaging system, the processing device 140 may generate the first image by performing the transformation operation. The transformation operation may include a transformation operation and an inverse transformation operation. For example, the processing device 140 may determine an initial image. Further, the processing device 140 may obtain a sampling image in a k-space by performing a transformation operation on the initial image. Further, the processing device 140 may obtain the first image by performing an inverse transformation operation based on the sampling data and the imaging data.

In some embodiments, the processing device 140 may perform the projection operation according to reconstruction techniques. Exemplary reconstruction techniques may include an algebraic reconstruction technique (ART), a simultaneous algebraic reconstruction technique (SART), a penalty weighted least squares (PWLS) technique, or the like, or any combination thereof. Merely by way of example, as described in connection with operation 410, the forward projection step and the back projection step may be performed according to Equation (1) and Equation (2). As another example, the transformation step and the inverse transformation step may be performed according to Equations (3)-(5), which are not repeated herein.

In some embodiments, feature information may be retained in the first image. Exemplary feature information may include gradient information, pixel information, grayscale information, or the like. In some embodiments, the imaging data may also include noise. The noise in the imaging data so acquired may be preserved and/or reflected in the first image generated based on the imaging data.

In 1130, the processing device 140 (e.g., the feature extraction module 920) may generate at least two intermediate images based on the first image.

In some embodiments, the at least two intermediate images may include a first intermediate image and a second intermediate image (also referred to as "base image"). The first intermediate image may include feature information (also referred to as "signal feature") of the first image, and the second intermediate image may have lower noise than the first image.

In some embodiments, the first intermediate image may be generated by extracting the feature information of the first image. The feature information may be described in terms of, e.g., gradient information, pixel information, grayscale information, or the like, or any combination thereof. The gradient information may be used to reflect boundary information relating to the subject (e.g., a specific portion, an organ, and/or a tissue of a patient). In some embodiments, the gradient information may be expressed in the form of a matrix. The pixel information may be used to reflect pixels (or voxels) in terms of, e.g., a pixel/voxel value, a location of each element, or the like, or a combination thereof, of the first image. The grayscale information may be used to reflect luminance (or brightness) information of image elements in the first image (e.g., a grayscale image). In some embodiments, the feature information of the first image may be expressed in the form of an image (or a matrix) (i.e., the first intermediate image).

In some embodiments, to extract the feature information of the first image, the processing device 140 may generate a feature map based on the first image. In some embodiments, to generate a feature map, the processing device 140 may obtain a second-order differential value and a pixel mean value of the first image. For example, the processing device 140 may obtain the second-order differential value by performing a second-order differential operation in the three-dimensional space. As described in connection with operation 420, the second-order differential operation may have a sharpening effect such that boundary information in the first image may be improved, e.g., the location of the boundary being more accurate, the contrast between the boundary and its vicinity being. That is, the second-order differential value may be used to reflect the gradient information. And the pixel mean value of the first image may be used to reflect the pixel information and the grayscale information. Further, the processing device 140 may generate the feature map based on the second-order differential value and the pixel mean value. In such cases, the feature map generated based on the second-order differential value and the pixel mean value of the first image may include the feature information of the first image. Further, the processing device 140 may determine the feature information of the first image based on the feature map. For example, the processing device 140 may determine the feature information from the feature map based on a feature extraction algorithm (e.g., a signal extraction algorithm).

In some embodiments, to extract the feature information of the first image, the processing device 140 may determine the feature information of the first image based on a first machine learning model. In some embodiments, the first machine learning model may be determined by training a preliminary first machine learning model based on a plurality of samples. Merely by way of example, the processing device 140 may pre-establish a preliminary first machine learning model for determining the feature information of the first image. Further, the processing device 140 may obtain the plurality of samples associated with a plurality of sample subjects. Each of the plurality of samples may include a sample first image and sample feature information of the sample first image. A training sample set may be determined based on the plurality of samples. The processing device 140 may further input the training sample set (e.g., with the sample feature information as a label) to train the preliminary first machine learning model. When a certain condition is satisfied (e.g., a certain count of iterations has been performed), a machine learning model so trained may be used as the first machine learning model for determining the feature information of the first image.

In some embodiments, the second intermediate image may be generated by performing a filtering operation on the first image. For example, to generate the second intermediate image, the processing device 140 may perform, based on a filtering algorithm, the filtering operation on the first image. The filtering algorithm may be used to reduce or remove the noise in the first image. Exemplary filtering algorithms may include a Gaussian filtering algorithm, a non-local mean (NLM) filtering algorithm, a block-matching and 3D (BM3D) filtering algorithm, or the like, or any combination thereof. In such cases, the second intermediate image may have lower noise than the first image.

In some embodiments, the second intermediate image may be generated by processing, based on a second machine learning model (also referred to as "neural network"), the first image. In some embodiments, the second machine learning model may be trained offline before the generation of the second intermediate image. In some embodiments, the second machine learning model may be generated according to a model training process. For example, the processing device 140 may obtain a training sample set including a plurality of sample image pairs. Each of the plurality of sample image pairs may include a first sample image and a second sample image of a same sample subject. The first sample image may have lower noise than the second sample image. Further, the processing device 140 may train a preliminary second machine learning model based on the training sample set. For example, the processing device 140 may train the preliminary second machine with the second sample image as an input sample and the first sample image as a target sample). When a certain condition is satisfied (e.g., a certain count of iterations has been performed), a machine learning model so trained may be used as the second machine learning model for determining the second intermediate image.

In some embodiments, the second machine learning model may be trained online concurrently with the generation of the second intermediate image. For example, the processing device 140 may generate, based on an initial image, a third image using the second machine learning model. The initial image may be obtained by the processing device 140 randomly. When generating the third image, the initial image may be used as an input of the second machine learning model, and the first image may be used as a target for training the second machine learning model. Further, the processing device 140 may determine loss information configured to assess a difference between the first image and the third image. Further, the processing device 140 may update the second machine learning model based on the loss information. For example, the processing device 140 may update parameters of the second machine learning model iteratively based on the loss information according to, for example, a backpropagation algorithm. When a termination condition is satisfied, the trained second machine learning model in the current iteration may be used as the updated second machine learning model. Exemplary termination conditions may include the noise in the third image is lower than or equal to a threshold, or a certain count of iterations have been performed. Further, the processing device 140 may generate, based on the first image, the third image using the updated second machine learning model. The third image generated by the updated second machine learning model may be designated as the second intermediate image.

In some embodiments, at least one of the at least two intermediate images may be generated based on a machine learning model. For example, if the first image includes relatively low noise, the image processing process may mainly focus on retaining and/or enhancing the feature information. In such cases, the first intermediate image may be generated based on the first machine learning model, and the second intermediate image may be generated by performing the filtering operation on the first image. As another example, in an image processing process for both retaining and/or enhancing the feature information and reducing or removing the noise, the first intermediate image may be generated based on the first machine learning model, and the second intermediate image may be generated based on the second machine learning model. As a further example, if the first image includes relatively high noise, the image processing process may mainly focus on reducing or removing the noise. In such cases, the first intermediate image may be generated by extracting the feature information of the first image, and the second intermediate image may be generated based on the second machine learning model.

In some embodiments, the machine learning model (e.g., the trained first machine learning model or the trained second machine learning model) may be stored in a memory or a storage device (e.g., the storage device 150) disclosed elsewhere in the present disclosure. The processing device 140 may retrieve the trained machine learning model from the memory or the storage device.

In 1140, the processing device 140 (e.g., the image reconstruction module 930) may generate, based on the first intermediate image and at least one of the first image or the second intermediate image, a target image (also referred to as "regularized image") of the subject.

In some embodiments, the imaging data may be acquired in an imaging process using a relatively high detected count. Accordingly, the first image may have relatively low noise. In such cases, the processing device 140 may generate the target image based on the first intermediate image and the first image. For example, the processing device 140 may determine a first weight for the first intermediate image, and determine a second weight for the first image. Further, the processing device 140 may generate the target image by combining, based on the first weight and the second weight, the first intermediate and the first image.

In some embodiments, the first weight may be larger than the second weight. As described in connection with operation 440, at least a portion of elements of the first weight may be larger than the corresponding elements of the second weight. For example, each element in the first weight may be larger than a corresponding element in the second weight. As another example, elements in the first weight corresponding to the boundary information may be larger than corresponding elements in the second weight. In such cases, the boundary information may be enhanced in the target image, and other portions of the target image may be filled by the first image.

In some embodiments, the imaging data may be acquired in an imaging process using a relatively low detected count. Accordingly, the first image may have relatively high noise. In such cases, the processing device 140 may generate the target image based on the first intermediate image and the second intermediate image. For example, the processing device 140 may determine a first weight for the first intermediate image, and determine a second weight for the second intermediate image. Further, the processing device 140 may generate the target image by combining, based on the first weight and the second weight, the first intermediate and the second intermediate image. In some embodiments, the first weight may be larger than the second weight. For example, each element in the first weight may be larger than a corresponding element in the second weight. As another example, elements in the first weight corresponding to the boundary information may be larger than corresponding elements in the second weight.

In some embodiments, the processing device 140 may update the target image according to an iterative operation including one or more iterations. In each current iteration, the target image generated in a previous iteration may be used to generate an updated target image in the current iteration. In some embodiments, the processing device 140 may update the target image iteratively until a termination condition is satisfied. Exemplary termination conditions may include a difference (e.g., a difference of corresponding pixel values) between the target images generated the previous iteration and the current iteration is in a certain range, a certain count of iterations have been performed, or the like, or any combination thereof. More descriptions regarding the iterative operation for updating the target image may be found elsewhere in the present disclosure. See, e.g., FIG. 12, and relevant descriptions thereof.

It should be noted that the above description of the process 1100 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the process 1100 may also include a training operation in which the machine learning models above may be generated. As another example, although a process for processing data relating to the imaging system is illustrated in process 1100, it should be understood that the method disclosed herein may also be applied to any other systems and/or devices for image processing.

Figure 12:
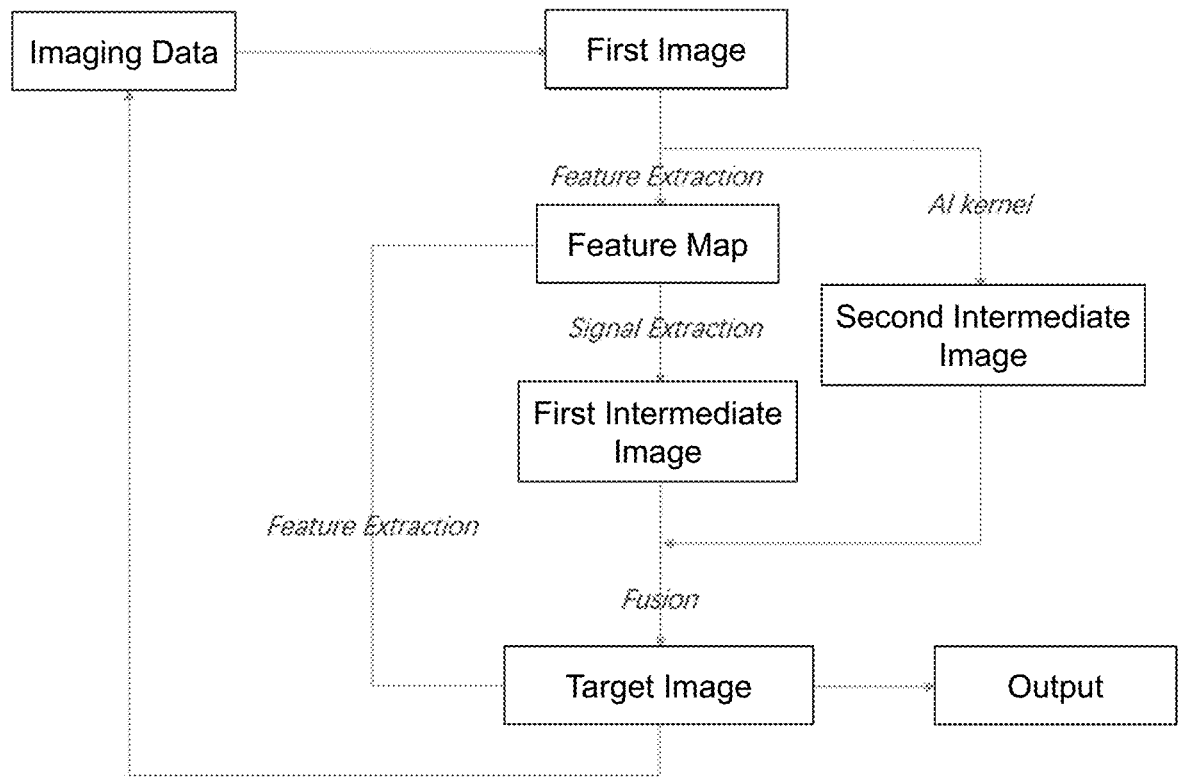
FIG. 12 is a schematic diagram illustrating an exemplary process for generating a target image according to some embodiments of the present disclosure.

FIG. 12 is a schematic diagram illustrating an exemplary process for generating a target image according to some embodiments of the present disclosure. In some embodiments, the process 1200 may be implemented by an imaging system (e.g., the imaging system 100). In some embodiments, the imaging system may be implemented by software and/or hardware. In some embodiments, at least part of the process 1200 may be performed by the processing device 140 (implemented in, for example, the computing device 200 shown in FIG. 2). For example, the process 1200 may be stored in a storage device (e.g., the storage device 150, the ROM 230, the RAM 240, the storage 390) in the form of instructions (e.g., an application), and invoked and/or executed by the processing device 140 (e.g., the processor 220 illustrated in FIG. 2, the CPU 340 illustrated in FIG. 3, one or more modules illustrated in FIG. 9 or FIG. 10).

In some embodiments, as illustrated in FIG. 12, the process 1200 may include an iterative operation including one or more iterations. In an initial iteration of the iterative operation, a first image may be generated based on imaging data of a subject. For example, the processing device 140 may generate, based on the imaging data and an initial image, the first image by performing a reconstruction operation. Further, at least two intermediate images may be generated based on the first image. The at least two intermediate images may include a first intermediate image and a second intermediate image. The first intermediate image may be generated by extracting feature information of the first image. For example, the processing device 140 may generate a feature map based on the first image (also referred to as "feature extraction"). Then the first intermediate image may be generated by determining the feature information of the first image based on the feature map (also referred to as "signal extraction"). The second intermediate image may be generated by processing, based on a second machine learning model (e.g., a second machine learning model in an AI kernel), the first image. Further, the first intermediate image and the second intermediate image may be fused to generate a target image.

The target image may be updated iteratively in the next iterations of the iterative operation. For example, in a current iteration, a previous target image generated in a previous iteration may be used as an updated initial image for generating an updated first image. Further, the updated first image may be used to generate at least two updated intermediate images. Further, the at least two updated intermediate images may be used to generate an updated target image in the current iteration. In such cases, the target image may be generated iteratively until a termination condition is satisfied. Exemplary termination conditions may include a difference (e.g., a difference of corresponding pixel values) between the target images generated in the previous iteration and the current iteration is in a certain range, a certain count of iterations have been performed, or the like, or any combination thereof.

In some embodiments, as described in connection with operation 430, the first machine learning model may be trained online concurrently with the generation of the first intermediate image. In some embodiments, the first machine learning model may be trained in each iteration of the iterative operation for updating the target image. In some embodiments, the first machine learning model may be trained in certain iterations of the iterative operation for updating the target image. Merely by way of example, the first machine learning model may be trained after a certain count of iterations (e.g., 4 iterations, 5 iterations, 6 iterations, etc.) are performed.

In some embodiments, as illustrated in FIG. 12, the first intermediate image may be generated according to an iterative operation. For example, in a current iteration, the previous target image generated in a previous iteration may be used as an updated feature map. Then an updated first intermediate image may be generated based on the previous target image. Further, the updated first intermediate image and an updated second intermediate image (e.g., generated based on the previous target image) may be used to generate an updated target image in the current iteration. In such cases, the feature map may be generated iteratively until a termination condition is satisfied. Exemplary termination conditions may include a certain count of iterations have been performed. If the termination condition is satisfied in the current iteration, the current target image may be output as the target image. According to the iterative operation, the target mage generated in the previous iteration may be used as the updated feature map for generating the updated first intermediate image. In such cases, more complete feature information may be retained in the target image generated according to the iterative operation.

In some embodiments, the present disclosure may also provide a computer-readable storage medium storing a computer program. When the computer program is executed by a processor (e.g., the processing device 140), an image processing method provided in the present disclosure may be implemented. The method may include generating a reconstructed image based on raw data (e.g., by sampling). Feature information of the raw data may be retained in the reconstructed image. The method may include processing the reconstructed image in two or more steps. The two or more steps may include extracting a signal feature and generating a base image. The signal feature and the base image may be combined to generate a regularized image. The method provided in the present disclosure may have less dependence on the neural network. Additionally, the method of the present disclosure may generate an accurate regularized image with lower noise.

In some embodiments, the present disclosure may also provide a regularized image reconstruction device. The regularized image reconstruction device may include a storage and a processor (e.g., the processing device 140). The storage may store executable instructions. The processing may execute the set of instructions to implement the method of the present disclosure. In some embodiments, regularized image reconstruction device may be set in the imaging system 100, or in the terminal device 130 or the processing device 140.

It should be noted that the above description of the iterative operation is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the first intermediate image may also be generated based on a first machine learning model. As another example, the second intermediate image may also be generated by performing a filtering operation on the first image.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this disclosure are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction performing system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for image processing, implemented on a computing device having at least one storage device storing a set of instructions, and at least one processor in communication with the at least one storage device, the method comprising:
   obtaining imaging data of a subject;
   generating a first image based on the imaging data;
   generating at least two intermediate images based on the first image, wherein
      the at least two intermediate images include a first intermediate image and a second intermediate image, the first intermediate image including feature information of the first image, and the second intermediate image having lower noise than the first image; and
   generating, by fusing the first intermediate image and at least one of the first image or the second intermediate image, a target image of the subject, including:
      determining a first weight for the first intermediate image;
      determining a second weight for the first image; and generating the target image by fusing, based on the first weight and the second weight, the first intermediate image and the first image.

2. The method of claim 1, wherein the generating a first image based on the imaging data includes:
generating the first image by performing, based on the imaging data, a projection operation.

3. The method of claim 1, wherein the generating a first image based on the imaging data includes:
generating the first image by performing, based on the imaging data, a transformation operation.

4. The method of claim 1, wherein the first intermediate image is generated by extracting the feature information of the first image.

5. The method of claim 4, wherein the feature information includes at least one of: gradient information, pixel information, or grayscale information.

6. The method of claim 4, wherein the extracting the feature information of the first image includes:
generating a feature map based on the first image; and
determining the feature information of the first image based on the feature map.

7. The method of claim 6, wherein the generating a feature map based on the first image includes:
obtaining a second-order differential value and a pixel mean value of the first image; and
generating the feature map based on the second-order differential value and the pixel mean value.

8. The method of claim 4, wherein the extracting the feature information of the first image includes:
determining the feature information of the first image based on a first machine learning model.

9. The method of claim 1, wherein the second intermediate image is generated by performing a filtering operation on the first image.

10. The method of claim 1, wherein the second intermediate image is generated by processing, based on a second machine learning model, the first image.

11. The method of claim 10, wherein the second machine learning model is generated according to a model training process including:
obtaining a training sample set including a plurality of sample image pairs, wherein each of the plurality of sample image pairs includes a first sample image and a second sample image of a same sample subject, the first sample image has lower noise than the second sample image; and
training a preliminary second machine learning model based on the training sample set.

12. The method of claim 10, wherein the generating the second intermediate image by processing, based on a second machine learning model, the first image includes:
generating, based on an initial image, a third image using the second machine learning model;
determining loss information between the first image and the third image;
updating the second machine learning model based on the loss information; and
generating, based on the first image, the third image using the updated second machine learning model.

13. The method of claim 1, wherein the first weight is larger than the second weight.

14. The method of claim 1, wherein the generating, by fusing the first intermediate image and at least one of the first image or the second intermediate image, a target image of the subject includes:
determining a first weight for the first intermediate image;
determining a second weight for the second intermediate image; and
generating the target image by fusing, based on the first weight and the second weight, the first intermediate image and the second intermediate image.

15. The method of claim 14, wherein the first weight is larger than the second weight.

16. The method of claim 1, further comprising updating the target image according to an iterative operation including one or more iterations.

17. A method for image processing, implemented on a computing device having at least one storage device storing a set of instructions, and at least one processor in communication with the at least one storage device, the method comprising:
obtaining imaging data of a subject;
generating a first image based on the imaging data;
generating a first intermediate image by extracting feature information of the first image;
generating a second intermediate image by processing the first image, the second intermediate image having lower noise than the first image; and
generating, by fusing the first intermediate image and at least one of the first image or the second intermediate image, a target image of the subject, including:
determining a first weight for the first intermediate image;
determining a second weight for the first image; and
generating the target image by fusing, based on the first weight and the second weight, the first intermediate image and the first image.

18. The method of claim 17, wherein the machine learning model is generated according to a model training process including:
obtaining a training sample set including a plurality of sample image pairs, wherein each of the plurality of sample image pairs includes a first sample image and a second sample image of a same sample subject, the first sample image has lower noise than the second sample image; and
training a preliminary machine learning model based on the training sample set.

19. A system for imaging processing, comprising:
at least one storage medium including a set of instructions; and
at least one processor in communication with the at least one storage medium, wherein when executing the set of instructions, the at least one processor is directed to cause the system to perform operations including:
obtaining imaging data of a subject;
generating a first image based on the imaging data;
generating at least two intermediate images based on the first image, wherein
the at least two intermediate images include a first intermediate image and a second intermediate image, the first intermediate image including feature information of the first image, and the second intermediate image having lower noise than the first image; and
generating, by fusing the first intermediate image and at least one of the first image or the second intermediate image, a target image of the subject, including:
determining a first weight for the first intermediate image;
determining a second weight for the first image; and generating the target image by fusing, based on the first weight and the second weight, the first intermediate image and the first image.

* * * * *